US011478272B2

(12) United States Patent
Humayun

(10) Patent No.: US 11,478,272 B2
(45) Date of Patent: Oct. 25, 2022

(54) INSTRUMENTS AND METHODS FOR THE IMPLANTATION OF CELL-SEEDED ULTRA-THIN SUBSTRATES

(71) Applicant: University of Southern California, Los Angeles, CA (US)

(72) Inventor: Mark S. Humayun, Glendale, CA (US)

(73) Assignee: University of Southern California, Los Angeles, CA (US)

(*) Notice: Subject to any disclaimer, the term of this patent is extended or adjusted under 35 U.S.C. 154(b) by 25 days.

(21) Appl. No.: 16/280,956

(22) Filed: Feb. 20, 2019

(65) Prior Publication Data
US 2019/0254705 A1 Aug. 22, 2019

Related U.S. Application Data

(60) Provisional application No. 62/633,002, filed on Feb. 20, 2018.

(51) Int. Cl.
*A61B 17/34* (2006.01)
*A61B 17/00* (2006.01)
*A61B 17/02* (2006.01)

(52) U.S. Cl.
CPC ...... *A61B 17/3468* (2013.01); *A61B 17/0057* (2013.01); *A61B 17/02* (2013.01);
(Continued)

(58) Field of Classification Search
CPC ...... A61B 17/3468; A61B 2017/00336; A61B 2017/00353; A61B 17/0057; A61B 17/02;
(Continued)

(56) References Cited

U.S. PATENT DOCUMENTS 4,957,505 A 9/1990 Mcdonald
6,616,683 B1 9/2003 Toth et al.
(Continued)

FOREIGN PATENT DOCUMENTS

EP 0363213 A2 * 4/1990 ........... A61F 2/1664
EP 2022415 A1 2/2009
(Continued)

OTHER PUBLICATIONS

PCT/US2019/018831 , "International Preliminary Report on Patentability", dated Sep. 3, 2020, 8 pages.
(Continued)

*Primary Examiner* — Katherine M Shi
*Assistant Examiner* — Mohammed S Adam
(74) *Attorney, Agent, or Firm* — Kilpatrick Townsend & Stockton LLP

(57) ABSTRACT

A surgical instrument, and methods for its use, is described that includes clamp heads that can be nestled within or extended from a tubular sheath by longitudinal movement of the clamp heads' tines with respect to the tubular sheath. One of the tines includes an arch that slides against a mouth and inside wall of the tubular sheath, causing the clamp heads to open or close. The clamp heads close lightly, to within a predetermined (or zero) distance from one another, gently grasp an ultrathin polymer substrate seeded with cells, and pulls it within the sheath such that the substrate curls and folds to protect the cells.

20 Claims, 19 Drawing Sheets

(52) U.S. Cl.
CPC ........... *A61B 2017/00265* (2013.01); *A61B 2017/00336* (2013.01); *A61B 2017/00353* (2013.01); *A61B 2017/00469* (2013.01); *A61B 2017/0225* (2013.01)

(58) Field of Classification Search
CPC ........... A61B 2017/00265; A61B 2017/00469; A61B 2017/0225; A61B 2017/305; A61F 9/0017
See application file for complete search history.

(56) References Cited

U.S. PATENT DOCUMENTS

| | | | |
|---|---|---|---|
| 8,579,887 B2 | 11/2013 | Hanlon et al. | |
| 9,907,604 B2 | 3/2018 | Hanlon et al. | |
| 2002/0165580 A1* | 11/2002 | Zwiefel | A61B 10/06 606/205 |
| 2007/0208422 A1* | 9/2007 | Walter | A61F 2/0095 623/5.11 |
| 2008/0294093 A1* | 11/2008 | Maeda | A61B 17/3468 604/60 |
| 2013/0211440 A1 | 8/2013 | Schwab et al. | |
| 2015/0032207 A1* | 1/2015 | Humayun | A61F 9/00736 623/3.1 |
| 2016/0074098 A1 | 3/2016 | Kappus et al. | |
| 2016/0256140 A1* | 9/2016 | Haack | A61B 17/29 |
| 2017/0086871 A1* | 3/2017 | Scheller | A61F 9/00727 |

FOREIGN PATENT DOCUMENTS

| | | |
|---|---|---|
| WO | 2012004592 A1 | 1/2012 |
| WO | 2012149468 A2 | 11/2012 |
| WO | 2013096453 A1 | 6/2013 |

OTHER PUBLICATIONS

PCT/US2019/018831, "International Search Report and Written Opinion", dated May 29, 2019, 9 pages.
EP19756532.8, "Extended European Search Report", dated Oct. 5, 2021, 7 pages.
SG11202011238S, "Written Opinion", dated Mar. 2, 2022, 8 pages.

* cited by examiner

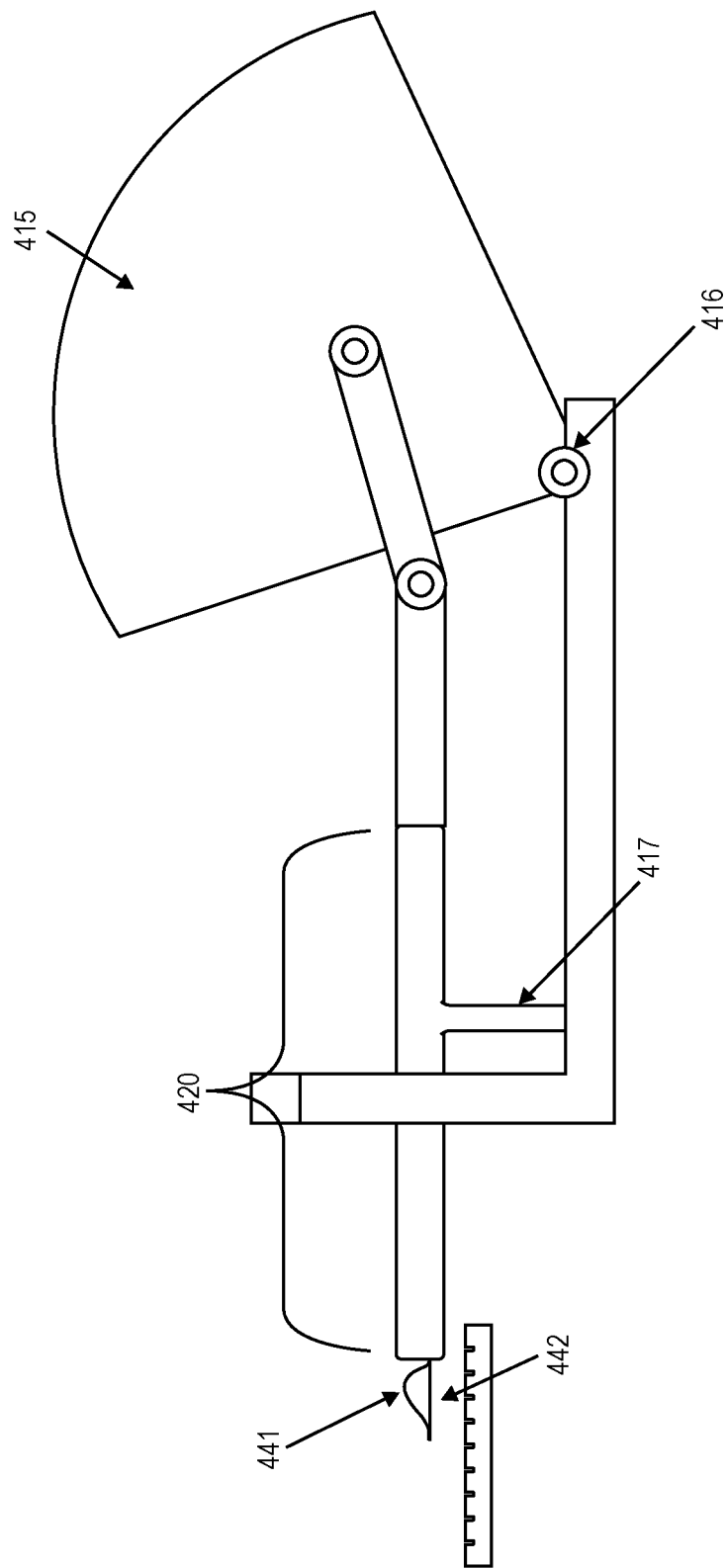

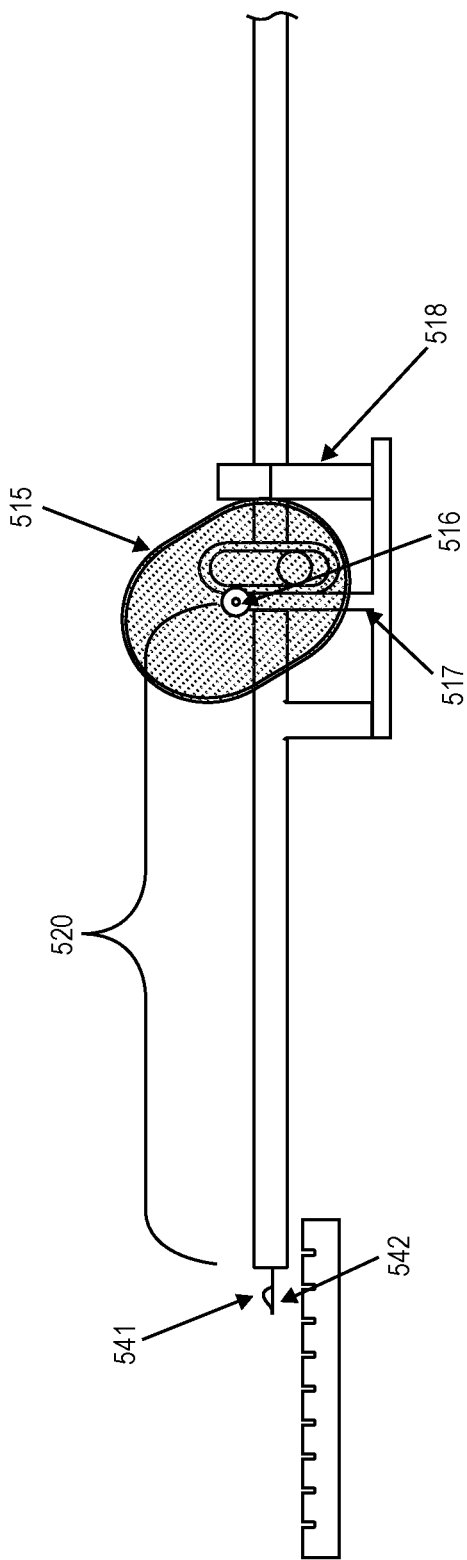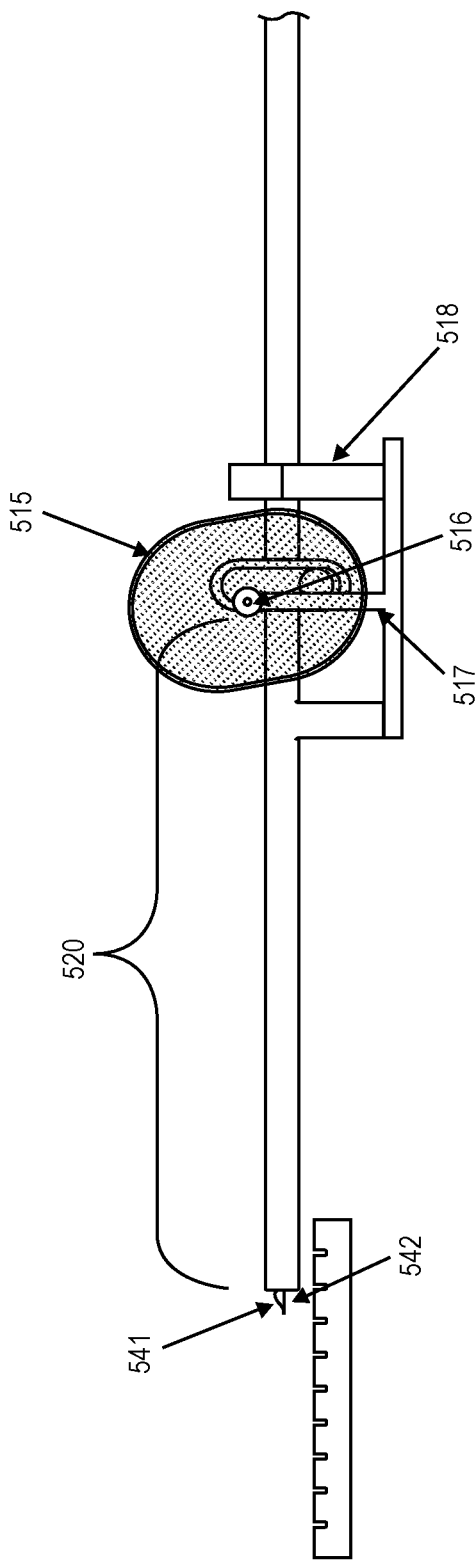

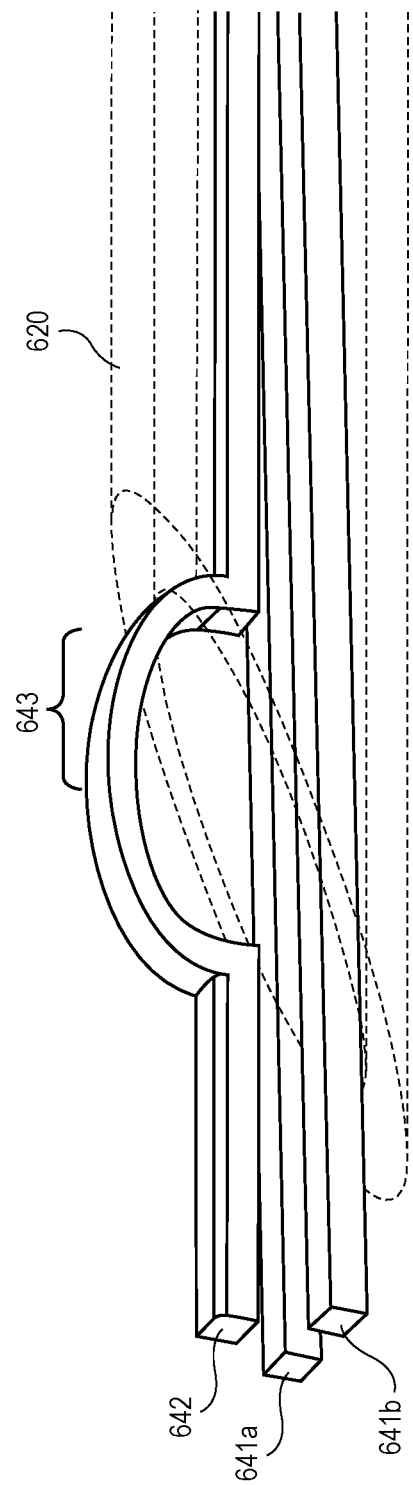

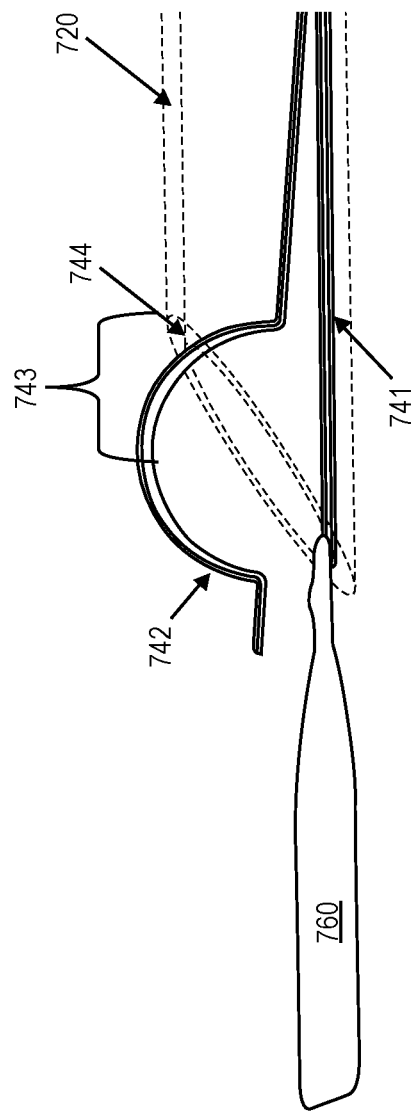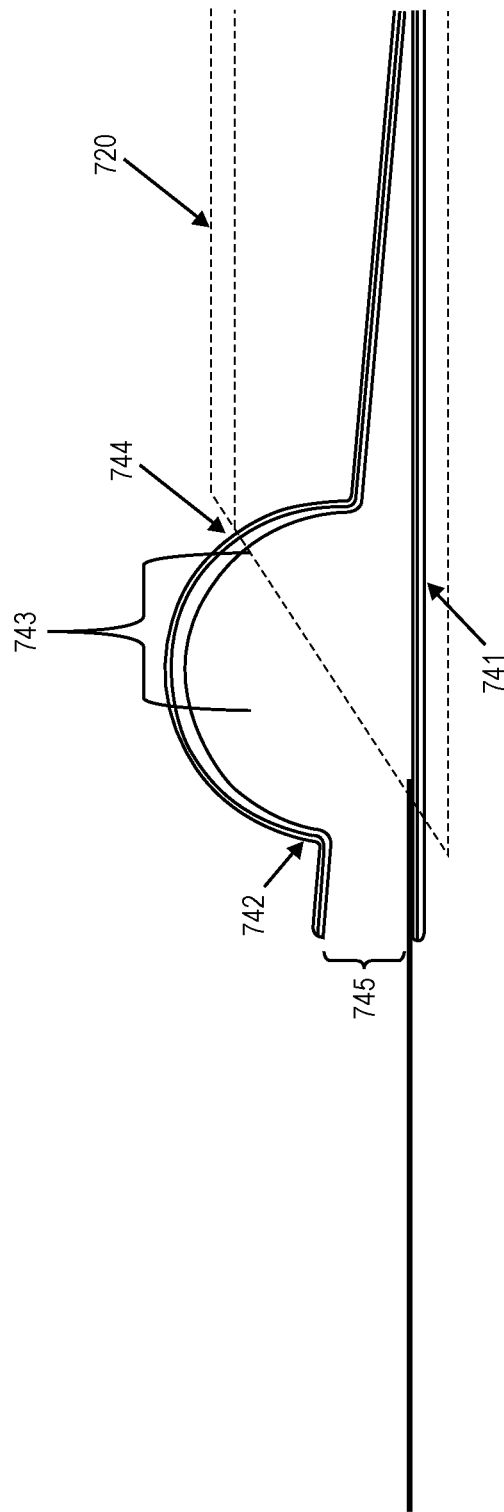

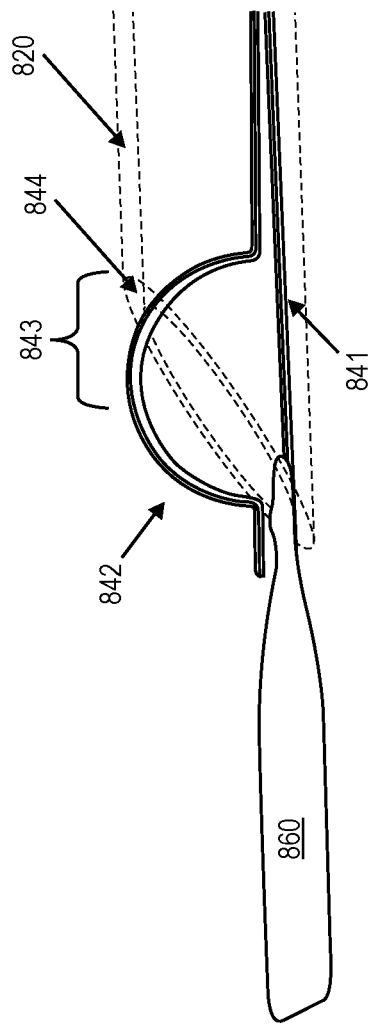
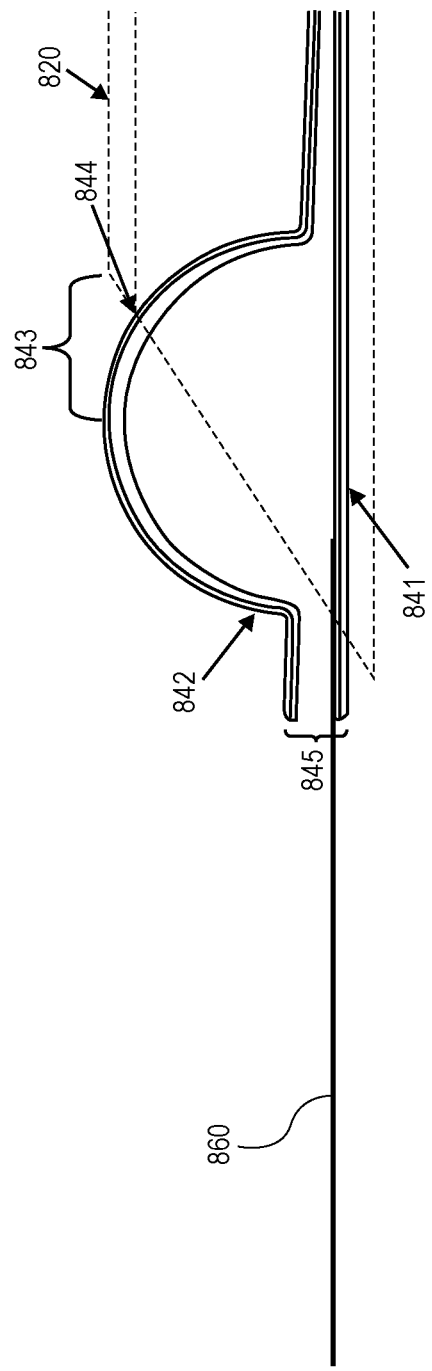

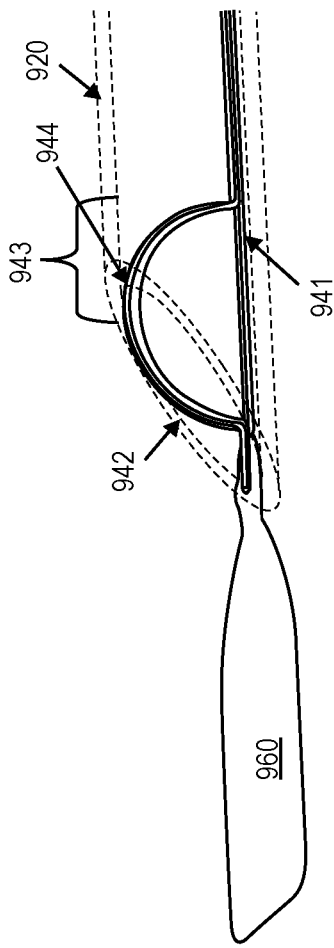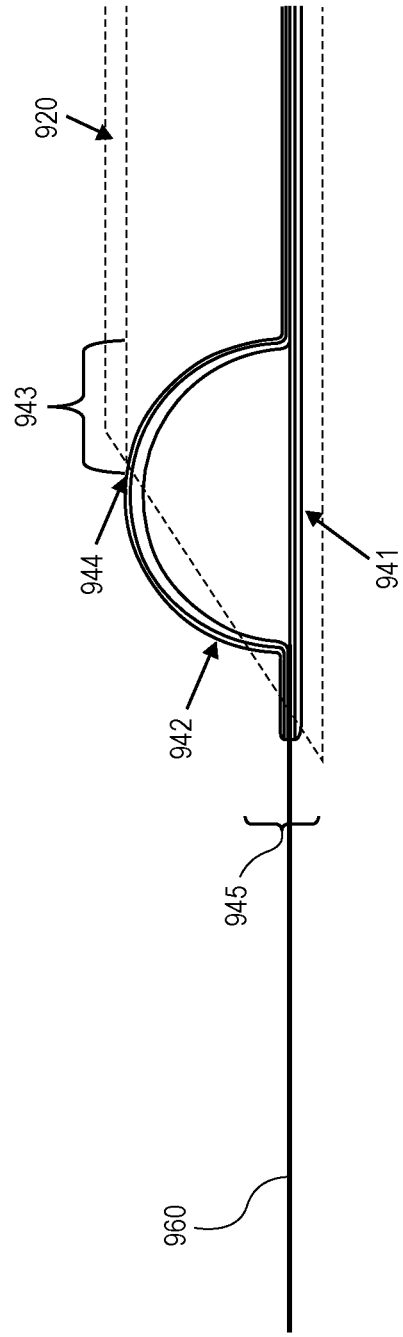

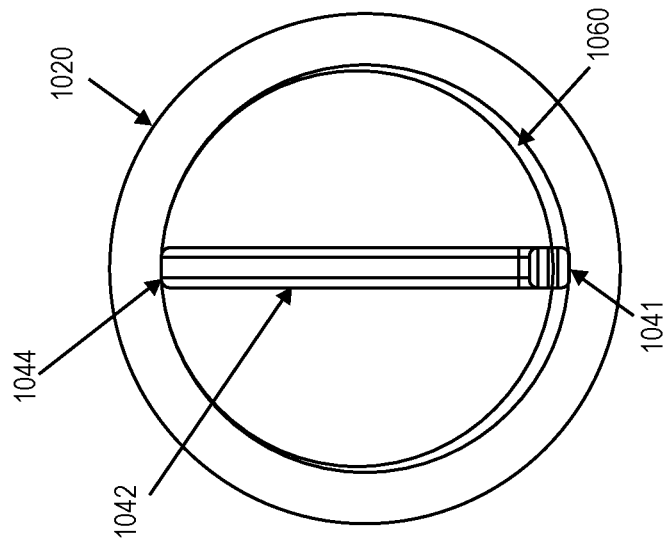
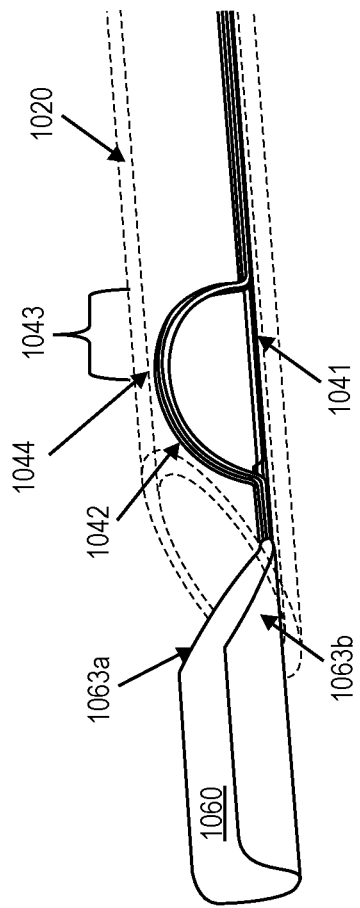
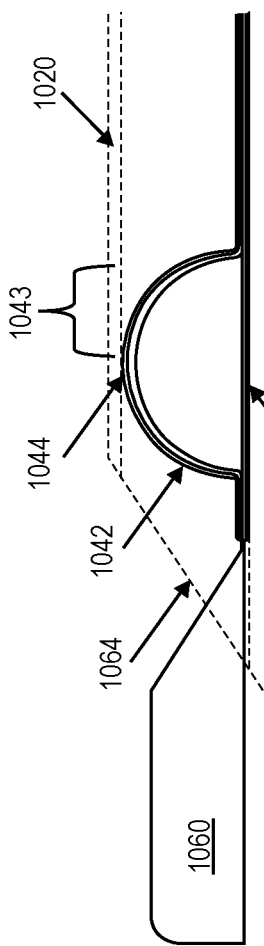
FIG. 10C
FIG. 10A
FIG. 10B

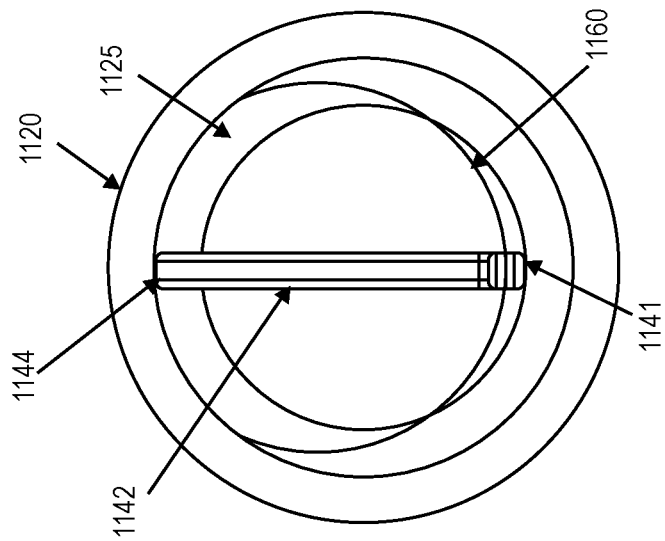
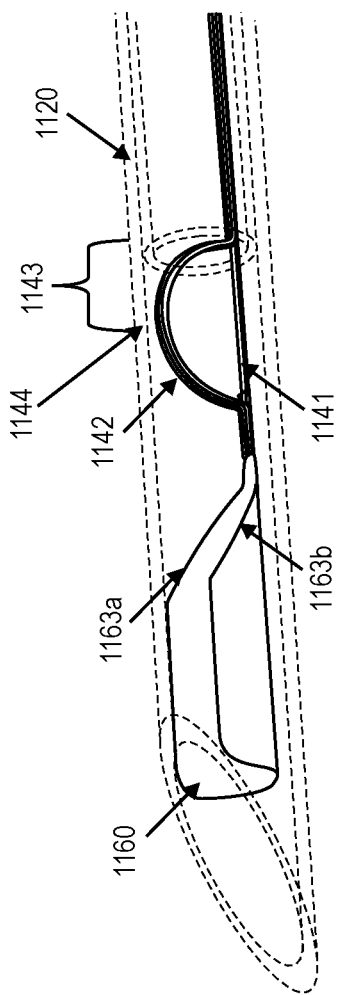
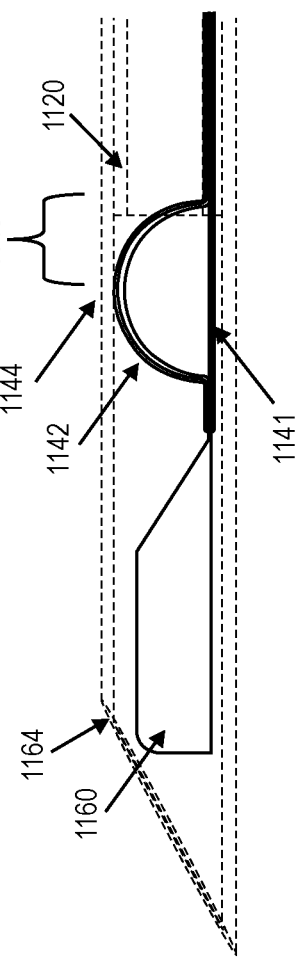
FIG. 11C
FIG. 11A
FIG. 11B

INSTRUMENTS AND METHODS FOR THE IMPLANTATION OF CELL-SEEDED ULTRA-THIN SUBSTRATES

CROSS-REFERENCES TO RELATED APPLICATIONS

This application claims the benefit of U.S. Provisional Application No. 62/633,002, filed Feb. 20, 2018, which is hereby incorporated by reference in its entirety for all purposes.

STATEMENT AS TO RIGHTS TO INVENTIONS MADE UNDER FEDERALLY SPONSORED RESEARCH AND DEVELOPMENT

Not Applicable

BACKGROUND

1. Field of Invention

The present application relates generally to instruments and methods for the implantation of ultrathin substrates into target tissues, the ultrathin substrates being suitable for seeding with stem cells for stem cell therapy, microbubbles, and infused gels for drug delivery, among other therapeutic treatments.

2. Description of Related Art

The scope of human disease that involves loss of or damage to cells is vast and includes, but is not limited to ocular disease, neurodegenerative disease, endocrine diseases, cancers, and cardiovascular disease. Cellular therapy involves the use of cells, and in some cases stem cells to treat diseased or damaged tissues. It is rapidly coming to the forefront of technologies that are poised to treat many diseases, in particular those that affect individuals who are non-responsive to traditional pharmacologic therapies.

In fact, many diseases that are candidates for application of cellular therapy are not fatal, but involve loss of normal physiological function. For example, ocular diseases often involve functional degeneration of various ocular tissues, which affects the vision, and thus the quality of life of numerous individuals.

The mammalian eye is a specialized sensory organ capable of converting incoming photons focused by anterior optics (cornea and lens) into a neurochemical signal. This process of phototransduction allows for sight by sending action potentials to higher cortical centers via the optic nerve. The retina of the eye comprises photoreceptors that are sensitive to various levels of light and interneurons that relay signals from the photoreceptors to the retinal ganglion cells. These photoreceptors are the most metabolically active cells in the eye (if not the body), and are supported metabolically and functionally by retinal pigmented epithelial (RPE) cells. These RPE cells are positioned in a monolayer in the eye and are critical to vision.

Numerous pathologies can compromise or entirely eliminate an individual's ability to perceive visual images, including trauma to the eye, infection, degeneration, vascular irregularities, and inflammatory problems. The central portion of the retina is known as the macula, which is responsible for central vision, fine visualization and color differentiation. The function of the macula may be adversely affected by wet or dry age related macular degeneration (AMD), diabetic macular edema, idiopathic choroidal neovascularization, high myopia macular degeneration, or advanced retinitis pigmentosa, among other pathologies.

AMD typically causes a loss of vision in the center of the visual field (the macula) because of damage to the retina. It is a major cause of visual impairment in older adults (>50 years of age). Macular degeneration occurs in "wet" and "dry" forms. In the dry form, cellular debris (drusen) accumulates between the retina and the choroid, the blood supply of the outer retina, which puts pressure on the retina, possibly leading to retinal detachment and loss of vision. In the more severe wet form of AMD newly formed blood vessels from the choroid infiltrate the space behind the macula, which causes death of photoreceptors and their supporting cells. In conjunction with the loss of functional cells in the eye, the newly formed blood vessels are fragile and often leak blood and interstitial fluid, which can further damage the macula.

While diseases that cause damage to specific cells or tissues are clear candidates for cellular therapy, there remains a need in the art for methods, substrate, and tools to improve the efficacy of cellular therapy.

BRIEF SUMMARY

Cells to be used in or on the delivered substrate are cultured on a completely fabricated and sterilized substrate. Substrates as described herein may be sterilized by gamma irradiation, ethylene oxide, autoclaving, ultraviolet (UV) sterilization, or other known procedures without degradation or damage. Cells are introduced to the sterilized substrate under sterile cell culture or sterile surgical suite conditions. The advantages of such processes are that optimally healthy and robust cells of a specific type (e.g. mature, differentiated, etc.) can be selected and deposited onto the substrate just prior to implantation, or further grown on the substrate prior to implantation. By further growing cells on a substrate prior to implantation, the substrate quality can be assessed by viewing cell growth uniformity, maturation, etc. Upon confirmation of not only cell growth, but substrate quality, the cell seeded substrate may be shipped for short term implantation or can be cryopreserved for later thaw and use.

In certain embodiments, the cell seeded substrate may be loaded onto a unique surgical instrument (e.g. a surgical introducer) prior to cryopreservation and before subsequent implantation of the implant by a surgeon.

Substrates in accordance with embodiments described herein may be delivered by various methods depending on the target tissue, all of which would benefit from the use of specialized delivery devices according to the shape, size, thickness, cell type, and overall thickness of the cell seeded substrate. Substrates may be delivered during an open surgical process, endoscopically, intravascularly, intramuscularly, stereotactically, or by other means known in the field for the particular target tissue.

In several embodiments, there is provided an instrument for the implantation of a substrate for transplanting (or subsequent seeding with a biological tissue, such as cells, a multi-cell type solution, matrix, time release gel, microbubbles, or any other treatment vehicle that can be placed on, in, within or anchored to the substrate) into a target tissue of a subject, comprising a handpiece comprising a proximal end and a distal end, the distal end comprising an orifice, a distal tubular sheath extending in a distal direction from said handpiece, an internal shaft having a proximal end and a distal end, wherein the distal-most portion of said internal shaft comprises a substrate interaction portion, a movement control mechanism (of either the tubular sheath, internal shaft, or both). In various embodiments the substrate interaction portion may consist of conventional forceps, scissors, or an orientation specific clasping mechanism (e.g. clamps, clasp, hitch, jaws, friction mount, or combination thereof).

In various embodiments, either the tubular sheath and/or the internal shaft may be configured to be longitudinally moveable comparatively to the tubular sheath and/or the internal shaft respectively to expose the internal shaft from the distal end. In some embodiments, the shaft movement control mechanism causes longitudinal movement of the internal shaft, wherein movement of the internal shaft in a proximal direction causes the distal-most portion of said internal shaft to retract within the distal most portion of the distal tubular sheath, and herein the retraction thereby causing said substrate interaction portion to release (e.g. forceps to close, scissors to cut, or orientation specific clasping mechanism to close), and wherein movement of the internal shaft in a distal direction causes the distal-most portion of the internal shaft to extend beyond the distal-most portion of the distal tubular sheath thereby causing the substrate interaction portion to actuate (e.g. forceps to open, scissors to open, or orientation specific clasping mechanism to open). These embodiments of retraction and extension of the internal shaft relative to a stationary tubular sheath are preferred where the implantable substrate must be pushed into a target tissue that would be irreversibly or additionally harmed by extending a larger diameter tubular sheath into such target tissue.

In another embodiment, the tubular sheath movement control mechanism causes longitudinal movement of the tubular sheath, wherein movement of the tubular sheath in a distal direction causes the distal-most portion of said internal shaft to be sheathed within the distal most portion of the distal tubular sheath, and herein the retraction thereby causing said substrate interaction portion to release (e.g. forceps to close, scissors to cut, or orientation specific clasping mechanism to close), and wherein the movement of the tubular sheath in a proximal direction causes the distal-most portion of the internal shaft to be unsheathed beyond the distal-most portion of the distal tubular sheath thereby causing the substrate interaction portion to actuate (e.g. forceps to open, scissors to open, or orientation specific clasping mechanism to open).

These embodiments of sheathing/unsheathing with a stationary internal shaft may be preferred in target tissues where the implantable substrate has limited longitudinal space freedom due to fragile neighboring structures that prefer the natural placement or unfolding only in latitudinal directions.

In several embodiments, two movement control mechanisms are used to induce the movements of sheathing/unsheathing of the tubular sheath and the retraction/extension of the internal shaft independently of each other. Alternatively, the movement control mechanisms may be hybridized onto one control mechanism in which a movement from a first position to the second position of the control mechanism allows for sheathing or unsheathing of the tubular sheath while the internal shaft is to be stationary and a movement from the second position to a third position of the control mechanism allows for the retraction or extension of the internal shaft while the tubular sheath is stationary. Alternatively, movement from a first position to the second position of the control mechanism may allow for the retraction or extension of the internal shaft while the tubular sheath is stationary and a movement from the second position to a third position of the control mechanism allows for the sheathing or unsheathing of the tubular sheath while the internal shaft is to be stationary.

In embodiments in which the substrate interaction portion is a forceps, the opening or closure of the forceps results in the respective release or grasping of a substrate. In certain embodiments the two forceps heads may be mechanically hinged. In other embodiments, the forceps comprise two tines movable in opposite direction relative to one another. In other embodiments, the forceps comprise one movable tine and one fixed tine. The tines may converge into one single tine at a proximal location and be separated distally in its normal state, only to close upon application of an external force on the movable tine. In several embodiments, one or more additional tines in various configurations may induce folding of the substrate upon releasing and grasping (e.g. one top tine and two bottom tines that are parallel and offset in a latitudinal direction to the left and right side causes the folding up of the left and right sides of the substrate when the substrate is grasped. In several embodiments, one or more tines consist of arches that interact with the inner circumference of the tubular sheath, thereby inducing opening and closing of the forceps as the point of interaction changes (e.g. a slope, curve, and wave) and pressure is applied to the movable tine by the tubular sheath. The point of interaction dictates the distance opening of the forceps (e.g. distance between two or more tines).

Unlike standard forceps with variable tolerances that tend to over-exert a closing force beyond that with 0 microns, when closed, in certain embodiments, the distance between the forceps during all points of interaction is greater than 0 microns but no less than a proportional thickness of the target ultra-thin substrate (e.g. 1 micron to 1000 microns). The proportional thickness of the target ultra-thin substrate being 20% or greater, 30% or greater, 40% or greater, 50% or greater, 60% or greater, 70% or greater, 80% or greater, 90% or greater, 100%. This limitation on the closing distance minimizes shear forces on the ultra-thin membranes which rip, tear, and/or fracture ultrathin membranes, thereby compromising its structural integrity and or creating debris by friction with the forceps' jaws.

In additional embodiments, the substrate may further include corresponding curved portions on the proximal side that interact with the taper of the tubular sheath (e.g. tapering of the cannula tip, much like a needle) that allow the substrate to fold like a non-overlapping taco tortilla as the substrate is retracted into the tubular sheath, thereby protecting the cell layers within. In many embodiments, the substrate width is ideally less than the inner circumference of the tubular sheath to prevent overlapping of the substrate when curled or otherwise folded within the tubular sheath. Such non-overlapping configuration prevents any treatment mechanism (e.g. cells, microbubbles, and drug) from being scraped off by the substrate folding onto itself.

In additional embodiments, the substrate interaction portion or tubular sheath has various arches and varying lengths to facilitate placement of the substrate in particular target tissue regions. For example, in ophthalmic implantations, natural variations in the axial length of the eye or the circumference of the eye may benefit from a slight curvature in the distal portion of the tubular sheath. Such curvature facilitates placement of the substrate in the sub-retinal space with a lower bleb, more posterior position and reduces the probability of retinal trauma during the delivery process, especially for eyes with longer than average axial lengths.

In several embodiments, the movement control mechanism comprises a slide mechanism. In several embodiments, the movement control mechanism comprises a friction wheel mechanism. In other embodiments, the movement control mechanism comprises one or more racks associated with the forceps and a gear mechanism that interacts with the racks. In yet another embodiment the movement control mechanism comprises a rocker wheel with a set pivot point. The movement control mechanism may or may not be on the handle of the instrument, but instead be controlled by a tethered or wireless control unit such as a foot pedal to be controlled by a surgeon.

Some embodiments further include tapering of the distal portion of the tubular sheath to optimize the delivery procedure by inducing the folding of a substrate into a "U" shape, further into a "C" shape, right before there is any overlap of the substrate, or until there is overlap of only the non-cell-seeded regions of the substrate. Such folding can gently decrease the lateral maximum dimension of the substrate, thereby reducing the surgical incision size required for implantation. This process also protects the substrate and any seeded layer of cells (monolayer or multilayer) during the insertion process from contact with external surfaces and forces.

In several embodiments, the instrument further comprises a reversibly releasable retaining mechanism to maintain the internal shaft in a retracted position. Such a mechanism beneficially secures the substrate interaction portion within the tubular sheath during transport and surgery preparation to prevent damage to the substrate interaction portion. In several embodiments, the reversibly releasable retaining mechanism comprising a retaining spring and switch.

In several embodiments, the instrument further comprises an injection pathway. In several embodiments, the injection pathway is configured to deliver a media from the handpiece to a target site at or near the distal-most portion of the internal shaft. In several embodiments, the media comprises a physiologically compatible substance. In some embodiments, the target tissue is ocular tissue and the media is perfluorocarbon. In several embodiments, the target tissue is selected from a group consisting of ocular tissue, cartilage, and cardiac tissue and the media is a bioadhesive. In several embodiments, the bioadhesive functions to assist in implanting the substrate by adhering the substrate (either temporarily or permanently) onto the host tissue. In other embodiments, the media is a carrier fluid that helps envelop and push out the substrate toward the target tissue site, thereby preventing damage from direct interaction with other surfaces (e.g. other tissues, inner portion of the tubular sheath, etc.) The media may additionally function as a required nutrient, growth, or enrichment medium tailored for the seeded cells by having one or more components of the culture solution to further maintain the desired cellular state by preventing further differentiation, maturation, or death of cells.

In several embodiments, there is also provided an instrument for the implantation of a substrate into a target tissue of a subject, comprising a handpiece comprising a proximal end and a distal end, a distally positioned substrate interaction portion comprising an apical and basal side and a shaft configured to couple said handpiece to said substrate interaction portion of the internal shaft. The distinct apical and basal sides are further created to minimally be affected by torsion or other twisting forces to maintain the desired orientation of the implant. The internal shaft may be strengthened or pre-biased to maintain the desired orientation by placement into one or more specific shaped (e.g. rectangular, square, triangular) slots throughout the handpiece (e.g. movement control mechanism, tubular sheath, etc.).

In several other embodiments, the instrument further comprises additional features that are broadly useful in surgical situations. Such features include but are not limited to endo-illumination, laser probes, cautery tip, hydrosuction, infusion, and lenses for continuous or periodic viewing/monitoring of the target site. Such additional features may be integrated into the same tubular sheath. In other embodiments, such additional features may be integrated into one or more parallel tubular sheaths containing one or more features within each.

To fully utilize the benefit of fully retractable internal shafts and various features, the tubular sheath may be clear or opaque to visualize the internal shaft features (e.g. the folded substrate within and distance until exposure and unrolling. Various materials may be used for various opacity (e.g. transparent or translucent) including but not limited to polyamide, polyimide and various other materials that are easily purchasable with very specific outer diameter (OD), internal diameter (ID), wall thickness, and tolerances. Many materials are ultra-smooth surfaces, chemically inert, sterilization tolerant.

Substrates

In several embodiments, the substrate is suitable for seeding with cells. In some embodiments, the substrate is suitable for seeding with stem cells. In several embodiments, the cells are RPE cells, precursors thereof, or derivatives thereof. In other embodiments, the substrate is suitable for seeding with one or more of corneal endothelial or epithelial cells, photoreceptor cells, trabecular meshwork, other ocular cells, precursors thereof, derivatives thereof, or combinations of any aforementioned cell types and complimentary cell types. In still additional embodiments, the substrate is suitable for seeding with one or more of chondroblasts, cardiac cells, precursors thereof, or derivatives thereof.

The substrate may be, without limitation, circular, oblong, or any shape customized to a specific individual patient pathology. Customization of substrates can be determined on a case-by-case basis by preliminarily measuring by electrophysiological testing, psychophysical testing (e.g. kinetic or static microperimetry), or various imaging modalities (e.g. ophthalmic examples: spectral-domain optical coherence tomography, fundus photography, fundus autofluorescense, or confocal scanning laser ophthalmoscopy (cSLO).

The substrates can have at least a portion manufactured to allow the selected therapeutic to anchor, on, in, or within the substrate. In embodiments where the therapeutic is cells, portions of the substrate may be regionally thinned, porous, or contain 3D structures to house cells in which adequate cell-to-cell communication and cell nutrient and waste exchange occurs. In embodiments where the therapeutic are microbubbles, the substrate is textured to allow the microbubbles to adhere. In embodiments where the therapeutic is a drug infused gel, the substrate may have wells or groves onto which the gel can be anchored.

A substrate can further benefit from having at least of part of its perimeter being structurally created or chemically treated to prevent cell growth. These cell-free portions of the substrate can be structurally distinct or visually differentiated to be the portion of the substrate to interact with the substrate interaction portion of the implantation instrument by thickness, color, texture, etc. In such embodiments, the implantation instrument does not disrupt the cells growing on the substrate growth surface, thereby maintaining the integrity and viability of cells during the implantation process.

In additional embodiments, the forceps are configured to reversibly interact with a substrate. In some embodiments, after interacting with a substrate, proximal longitudinal movement of the movement control mechanism causes retraction of the inner shaft resulting in contact between the outer edges of the substrate and the inner portion of the tubular sheath, thereby inducing the substrate to roll into a cylindrical shape (e.g. "U"-shape, "C"-shape, "V-shape", etc.). In some embodiments, distal longitudinal movement of the movement control mechanism causes the outer edges of the substrate to move distally beyond the tubular sheath, thereby allowing the rolled support to unroll and return to its original configuration (e.g. flat or naturally biased to a curvature of the target implant tissue site. In several embodiments, the substrate is cell-seeded, and wherein the cell-seeded substrate rolls in conjunction with the substrate support, but to a degree that does not allow the cell-seeded surfaces to roll onto one another.

In several embodiments, the substrate interaction portion of the inner shaft further includes a substrate supporting platform that functions to provide a "resting place" for the substrate during the implantation process. In several embodiments, the substrate supporting platform comprises a plurality of substrate barriers on the apical side of the platform. Taken together, such barriers provide a region in which a substrate (either pre-seeded with cells or ready to be seeded) is positioned and protected during the process of implantation into a target tissue. In several embodiments, the protection is from the shear forces that the substrate is exposed to during implantation (e.g., the flow of blood or ocular fluid across the implant). In several embodiments, the substrate is protected by the barriers from the contact with tissues that surround the target implantation site. In some embodiments, the barriers are positioned at or near the lateral edges of the platform, in order to accommodate a substrate of a certain desired size.

The substrate interaction portion of the internal shaft may further be modified to releasably grasp various different substrates while maintaining the cell-seeded substrate's desired orientation for implantation.

The substrate interaction portion of the internal shaft may further allow for an optional mechanism to detach the cell layer(s) from the substrate during implantation, thereby implanting only the cell layer into the target site and withdrawing the substrate prior to completion of the surgical procedure. The substrate may further include two portions: first the implant portion consisting of a cell layer with minimal scaffolding which may be preferably made of a biodegradable material, and second a sturdier substrate platform which is used to roll the cell layer and protect the cell layer from mechanical stresses during implantation. The minimal scaffolding of the first portion may beneficially be biodegradable and absorbed into the body after months or years once the cell layer has adaptably assimilates into the target tissue site.

In one embodiment, the implant portion of the substrate is located in the distal portion and can be mechanically separated from the substrate platform portion upon unrolling and placement. The separation may be completed by manipulating the substrate interaction portion to tear along pre-made perforations in the substrate or by using a flushing step of a carrier fluid to provide a tearing force. In another embodiment, multiples of the substrate may be loaded onto the insertion tool and be implanted in either one or more chained pieces or separated by tearing along pre-made perforations between the substrates.

In yet another embodiment, the implant portion of the substrate is located on the apical portion and can be mechanically separated from the basal substrate platform portion. The separation may be completed by manipulating the substrate interaction portion much like a spatula to separate the apical and basal portions and selectively withdrawing the bottom substrate platform portion into the tubular sheath. Alternatively, to separate at pre-made microperforations by pulling or using a cutting feature.

A variety of materials may be used to fabricate the substrate disclosed herein. In some embodiments, the substrates are biodegradable while in other embodiments, the substrates are non-biodegradable. In still other embodiments, a portion of the substrate is biodegradable while another portion is not. In several embodiments, the biodegradable portions of the substrates can be fabricated to degrade at a known rate. Such biodegradable materials include any suitable material that degrades or erodes over time when placed in the human or animal body. Accordingly, as the term is used herein, biodegradable material includes bioerodible materials.

Pairing of Instrument and Substrate

In some embodiments, the instrument and substrate may uniquely be made to pair with each other. In one embodiment, the substrate has an orientation identifier (e.g. a bump on the right side of the handle/forceps interaction portion to show the substrate is oriented correctly with the apical cell seeded surface on top). The forceps may additionally have matching small bump on the right side of one or more of the tines to show that bump should be on the right for both the substrate and the tines. Such bump alignment may also be used to ensure correct position when grasping/clamping the substrate.

In another embodiment, the substrate handle portion may consist of one or more openings through which the upper and lower tines may interact through. Not only does this allow for correct alignment to ensure correct positioning when grasping/clamping the substrate, the interaction may be used to close a circuit if the tines are made of a conductive material. Such closed circuit may trigger a light or sound to convey to the user that the substrate is secure. A ball/hitch type configuration can be used as well as other corresponding shapes.

BRIEF DESCRIPTION OF THE DRAWINGS

FIG. 4A illustrates an extended configuration of a rocker wheel control mechanism in accordance with an embodiment.

FIG. 5A illustrates an extended configuration of an oblong wheel control mechanism in accordance with an embodiment.

FIG. 5B illustrates an intermediate configuration of an oblong wheel control mechanism of FIG. 5A.

FIG. 6 illustrates multiple bottom tines of forceps in accordance with an embodiment.

FIG. 7A is an orthogonal view of an extended instrument in accordance with an embodiment.

FIG. 7B is a side view of the extended instrument of FIG. 7A.

FIG. 8A is an orthogonal view of an intermediate extended instrument in accordance with an embodiment.

FIG. 8B is a side view of the intermediate extended instrument of FIG. 8A.

FIG. 9A is an orthogonal view of an instrument grasping in accordance with an embodiment.

FIG. 9B is a side view of the instrument grasping of FIG. 9A.

FIG. 10A is an orthogonal view of an intermediately retracted instrument in accordance with an embodiment.

FIG. 10B is a side view of the intermediately retracted instrument of FIG. 10A.

FIG. 10C is an end view of the intermediately retracted instrument of FIG. 10A.

FIG. 11A is an orthogonal view of a fully retracted instrument in accordance with an embodiment.

FIG. 11B is a side view of the fully retracted instrument of FIG. 11A.

FIG. 11C is an end view of the fully retracted instrument of FIG. 11A.

DETAILED DESCRIPTION

Surgical instruments are disclosed that include clamp heads that nestle within a tubular sheath but be activated to extend out an end of the sheath. At least one tine of the clamp heads includes an arch that slides against the enclosing tubular sheath as it is retracted within, causing the tine to move with respect to the other tine(s). The clamp heads draw closed to within a predetermined nonzero, or zero, distance from one another in order to grasp a delicate substrate. The substrate is then drawn into the tubular sheath, folding its edges up and around to protect cells, microbubbles, or other therapeutic elements on the substrate.

Figure 1:
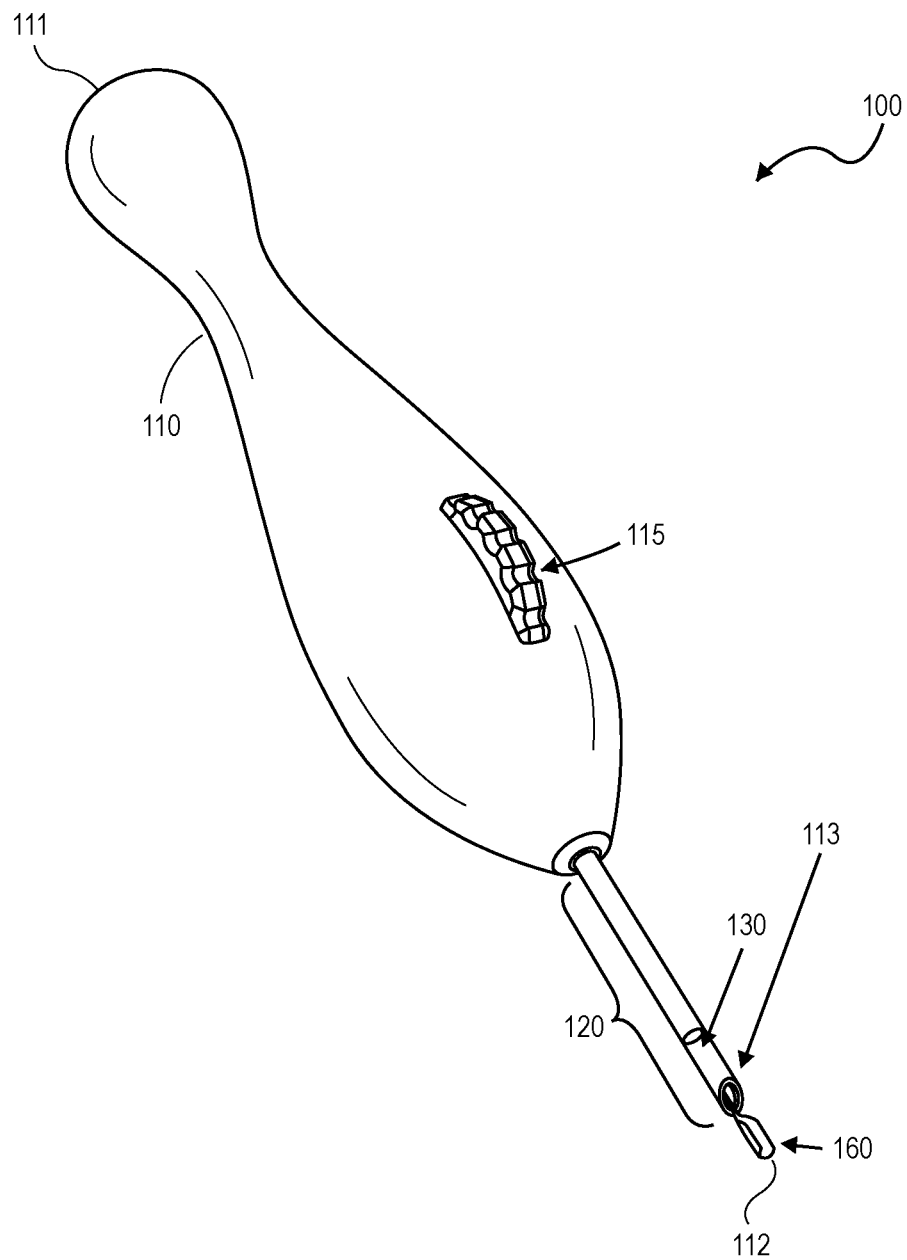
FIG. 1. is an orthogonal view of an instrument using a wheel for the movement control mechanism in accordance with an embodiment.

FIG. 1 shows a non-limiting example of such an instrument. The instrument 100 for the implantation of a substrate 160 for transplanting (or subsequent seeding with a biological tissue, such as cells, a multi-cell type solution, matrix, time release gel, microbubbles, or any other treatment vehicle that can be placed on or anchored to the substrate) into a target tissue of a subject, comprising a handpiece 110 comprising a proximal end 111 and a distal end 112, the distal end 112 comprising an orifice 113, a tubular sheath 120 extending in a distal direction from said handpiece 110, an internal shaft 130 having a proximal end and a distal end, wherein the distal-most portion of said internal shaft comprises a substrate interaction portion comprising clamp heads, a movement control mechanism 115 (of either the tubular sheath, internal shaft, or both). In various embodiments the clamp heads may function as conventional forceps, scissors, or an orientation specific clasping mechanism (e.g. clamp, clasp, hitch, jaws, friction mount, or combination thereof).

In various embodiments, either the tubular sheath 120 and/or the internal 130 shaft may be configured to be longitudinally moveable comparatively to the tubular sheath 120 and/or the internal shaft 130 respectively to expose the distal end of the internal shaft 130 from the distal end of the tubular sheath 120. In some embodiments, the shaft movement control mechanism 115 causes longitudinal movement of the internal shaft 130.

Movement of the internal shaft 130 in a proximal direction causes the distal-most portion of said internal shaft 130 to retract within the distal most portion of the distal tubular sheath 120, and herein the retraction thereby causing said clamp heads to close (e.g. forceps to close, scissors to cut, or orientation specific clasping mechanism to close). Movement of the internal shaft 130 in an opposite, distal direction causes the distal-most portion of the internal shaft 130 to extend beyond the distal-most portion of the tubular sheath 120 thereby causing the clamp heads to actuate (e.g. forceps to open, scissors to open, or orientation specific clasping mechanism to open). These embodiments of retraction and extension of the internal shaft 130 relative to a stationary tubular sheath 120 are preferred where the implantable substrate must be pushed into a target tissue that would be irreversibly or additionally harmed by extending a larger diameter tubular sheath into such target tissue.

In another embodiment, the tubular sheath movement control mechanism 115 causes longitudinal movement of the tubular sheath 120.

Movement of the tubular sheath 120 in a distal direction causes the distal-most portion of said internal shaft 130 to be sheathed within the distal most portion of the distal tubular sheath 120, and herein the retraction thereby causing said clamp heads to release (e.g. forceps to close, scissors to cut, or orientation specific clasping mechanism to close), and wherein the movement of the tubular sheath 120 in a proximal direction causes the distal-most portion of the internal shaft 130 to be unsheathed beyond the distal-most portion of the distal tubular sheath 120 thereby causing the clamp heads to actuate (e.g. forceps to open, scissors to open, or orientation specific clasping mechanism to open). These embodiments of sheathing/unsheathing with a stationary internal shaft may be preferred in target tissues where the implantable substrate has limited longitudinal space freedom due to fragile neighboring structures that prefer the natural placement or unfolding only in latitudinal directions.

In several embodiments, two movement control mechanisms are used to induce the movements of sheathing/unsheathing of the tubular sheath and the retraction/extension of the internal shaft independently of each other. Alternatively, the movement control mechanisms may be hybridized onto one control mechanism, such as movement control mechanism 115, in which a movement from a first position to the second position of the control mechanism allows for sheathing or unsheathing of the tubular sheath 120 while the internal shaft 130 is stationary and a movement from the second position to a third position of the control mechanism allows for the retraction or extension of the internal shaft 130 while the tubular sheath 120 is stationary. Alternatively, movement from a first position to the second position of the control mechanism may allow for the retraction or extension of the internal shaft 130 while the tubular sheath 120 is stationary and a movement from the second position to a third position of the control mechanism allows for the sheathing or unsheathing of the tubular sheath 120 while the internal shaft 130 is stationary.

Figure 2:
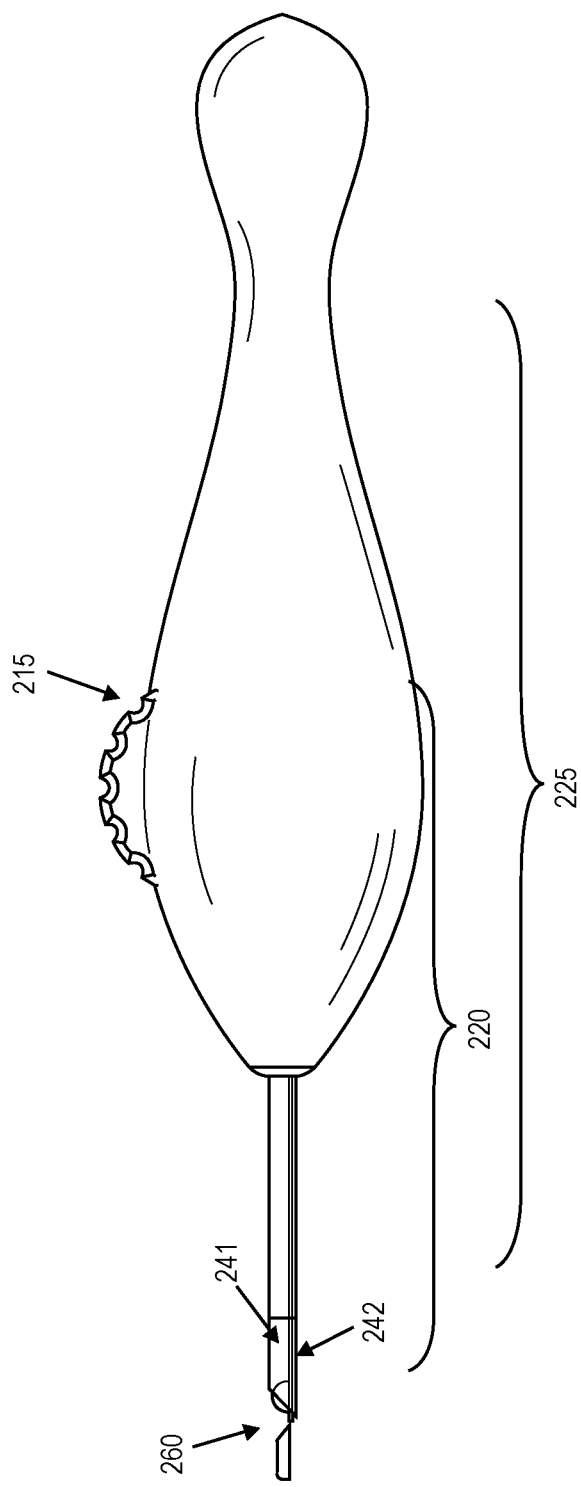
FIG. 2. is a side view of the instrument of FIG. 1.

FIG. 2. shows a side view of an embodiment using a wheel for the movement control mechanism 215. Two clamp heads 241 and 242 are shown to be exposed beyond the tubular sheath distal portion. In certain embodiments a stationary second inner tubular sheath 225, which extends well within the handpiece, surrounds a portion of the internal shaft to provided additional rigidity, but does not interact with the clamp heads 241 and 242. The second inner tubular sheath 225 may also have a smaller inner diameter and function as a stopper to prevent the clamp heads from retracting beyond a certain point.

In some embodiments, the second inner tubular sheath 225 may be used as an injection pathway configured to deliver media from the handpiece to a target site at or near the distal most portion of the internal shaft. Furthermore, the media may be a modular media cartridge to be added to the instrument. An actuation mechanism for the media may be built into the instrument (e.g. a button to actuate pressure) or a tethered mechanism may be connected near the cartridge for actuation. By having translucent or transparent tubular sheaths 230, 225, the position of the substrate and any media flowing through the sheaths can be monitored throughout the procedure.

Figure 3:
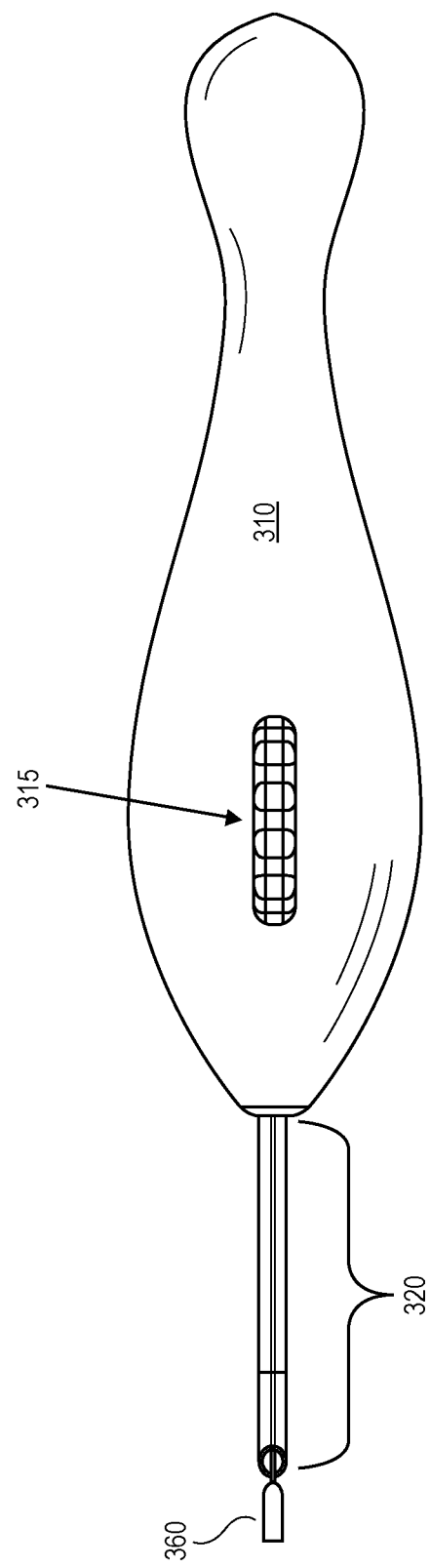
FIG. 3 is a top view of the instrument of FIG. 1.

FIG. 3 shows a top view of an embodiment using a wheel for the movement control mechanism 315. Outer tubular sheath 320 extends from handpiece 310. Substrate 360 is shown gripped just past the distal portion of tubular sheath 320, ready to be pulled within the sheath or implanted within a subject.

Figure 4B:
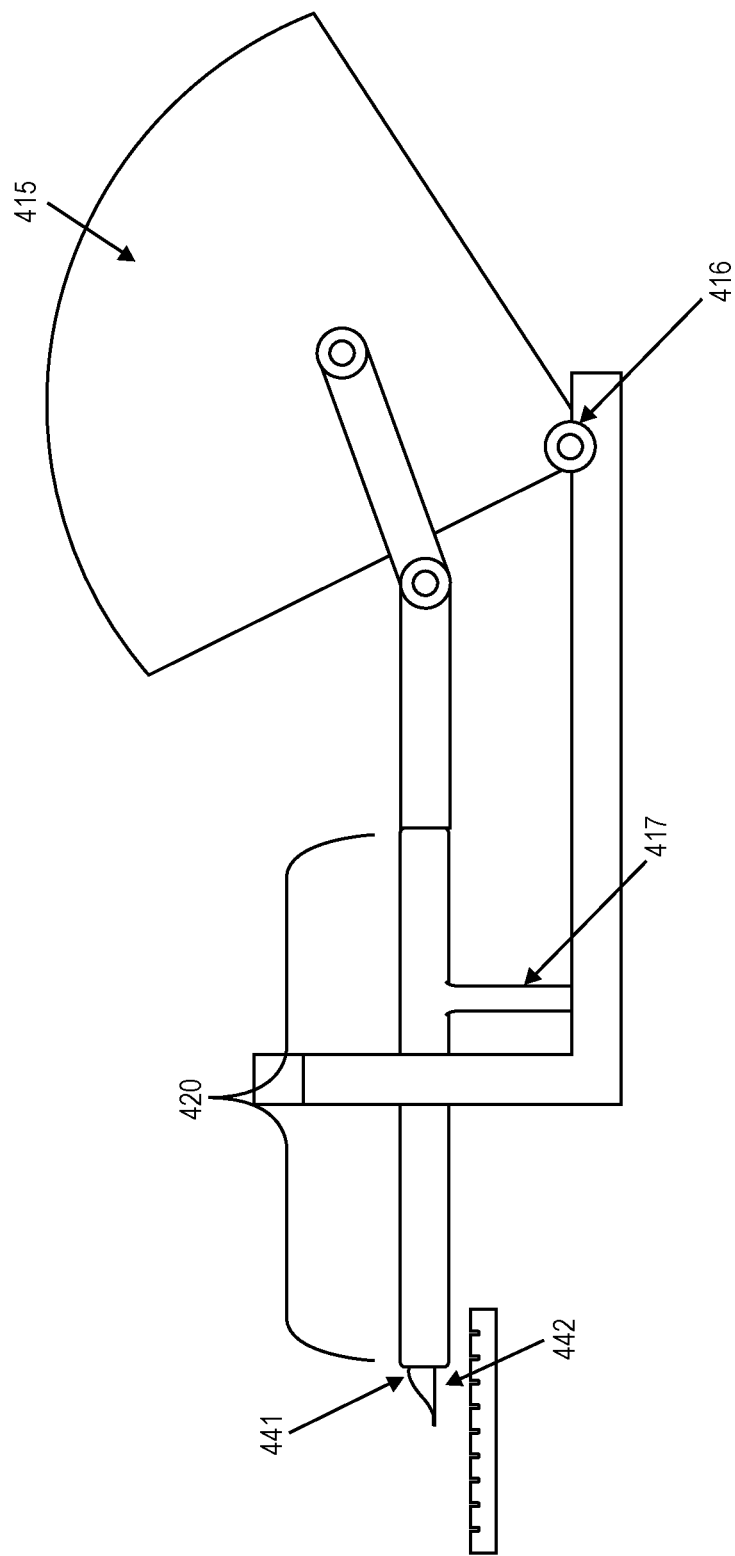
FIG. 4B illustrates an intermediate configuration of the rocker wheel control mechanism of FIG. 4A.
Figure 4C:
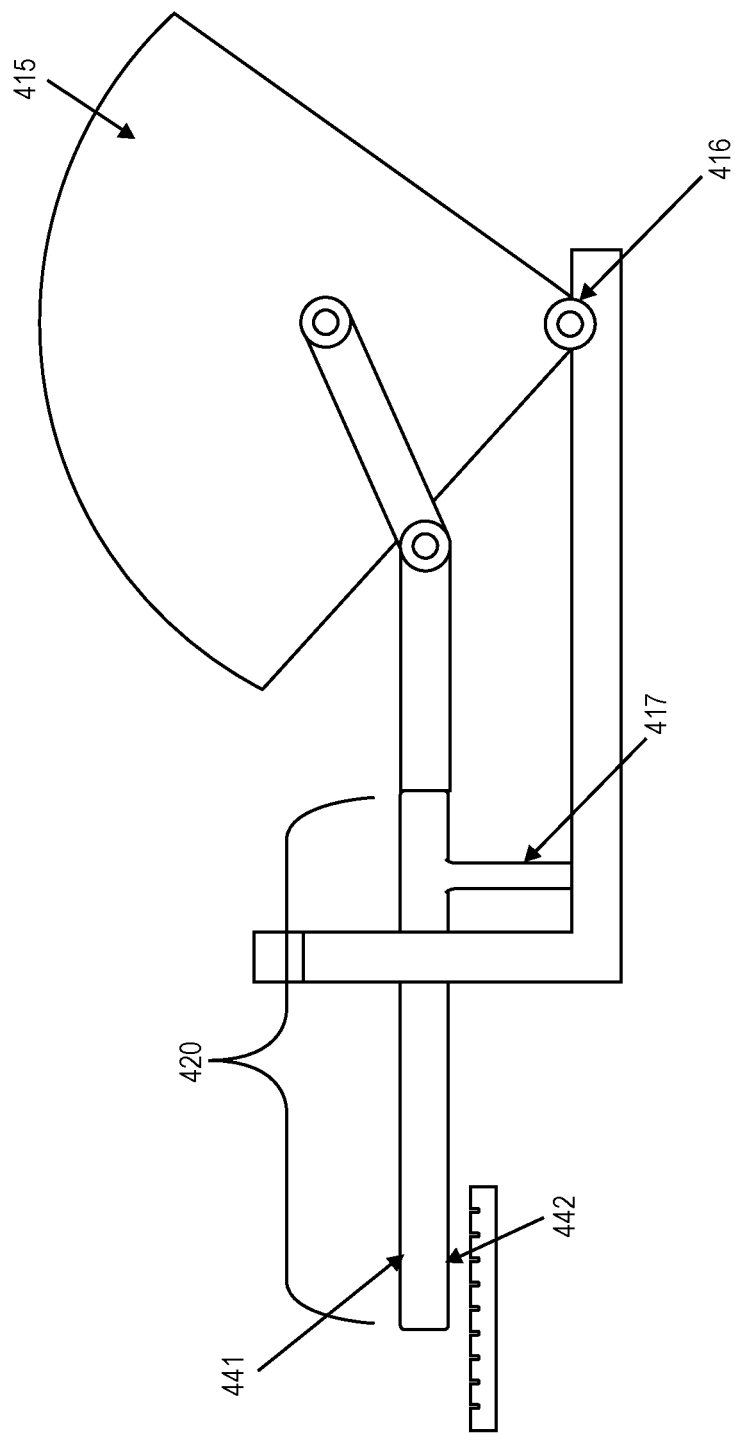
FIG. 4C illustrates an unextended configuration of the rocker wheel control mechanism of FIG. 4A.

FIGS. 4A-4C. shows an embodiment using a rocker wheel. For clarity, the housing and other surrounding elements are not shown. A movement control mechanism 415 moves tubular sheath 420. The internal shaft to which the two clamp heads 441 and 442 are connected is anchored to the housing by a perpendicular holder 417. Therefore, the clamp heads do not move longitudinally when the rocker wheel is actuated. To focus on the mechanical functionality of the rotary motion being converted to a straight-line motion, the handle portion has been removed and the mechanism simplified. The rocker wheel configuration requires a pivot pin 416 to act as a fulcrum point for the extension and retraction action as the rocker wheel is moved in a proximal and distal fashion.

FIG. 4A shows the two clamp heads 441 and 442 exposed beyond the tubular sheath as the rocker wheel mechanism is in the open position.

FIG. 4B shows the distal movement of the rocker wheel 415 moving the tubular sheath 420 in a distal direction, thereby partially covering the two clamp heads 441 and 442.

FIG. 4C shows the further distal movement of the rocker wheel 415 moving the tubular sheath 420 in a further distal direction, thereby fully covering the two clamp heads 441 and 442.

Figure 5C:
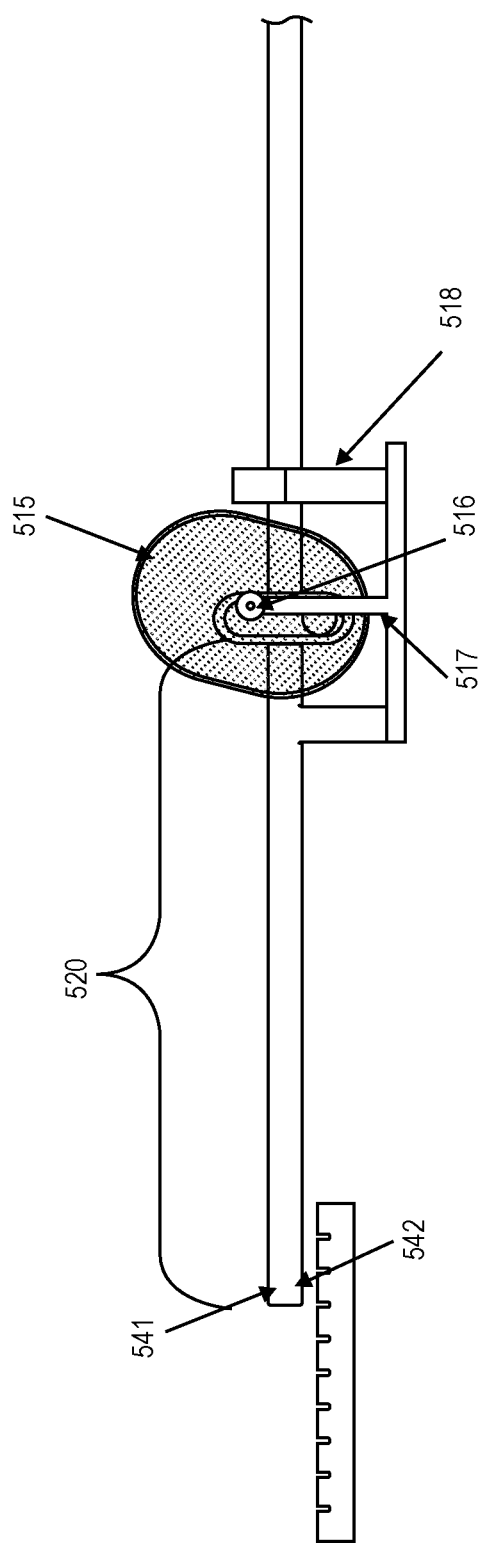
FIG. 5C illustrates an intermediate configuration of an oblong wheel control mechanism of FIG. 5A.

FIGS. 5A-5C. shows an embodiment using an oblong wheel for the movement control mechanism 515 to move the tubular sheath 520. For clarity, the housing and other surrounding elements are not shown. The internal shaft to which the two clamp heads 541 and 542 are connected is anchored to the housing by a perpendicular holder 517. Therefore, the clamp heads do not move longitudinally when the oblong wheel is actuated. An oblong shape is beneficial in allowing a limiting wall structure 518 to limit the distance of the wheel movement. Without the limiting wall structure 518, continuous movement of the oblong wheel 515 could result in a continuous cycle of distal and proximal movement of the tubular sheath 520. To focus on the mechanical functionality of the rotary motion being converted to a straight-line motion, the handle portion has been removed and the mechanism simplified. The oblong wheel configuration requires a pivot pin 516 to act as a fulcrum point for the extension and retraction action as the rocker wheel is moved in a proximal and distal fashion.

FIG. 5A shows the two clamp heads 541 and 542 exposed beyond the tubular sheath as the rocker wheel mechanism is in the open position.

FIG. 5B shows the distal movement of the rocker wheel 515 moving the tubular sheath 520 in a distal direction, thereby partially covering the two clamp heads 541 and 542.

FIG. 5C shows the further distal movement of the rocker wheel 515 moving the tubular sheath 520 in a further distal direction, thereby fully covering the two clamp heads 541 and 542.

In various other embodiments, other known mechanisms of translating rotary motion to a straight-line motion may be used. Common designs include a slider-crank mechanism and an eccentric-and-rod mechanism.

In various other embodiments, a linear slider may be used as the movement control mechanism 515. In these embodiments, a gear ratio is preferable that makes the tubular sheath 520 movement a fractional distance compared to the linear movement of the linear slider, thereby allowing minute changes that allow for gentle grasping and slow folding/unfolding of an ultra-thin substrate without tearing.

In some embodiments, the clamp heads function as a forceps, the opening or closure of the forceps results in the respective release or grasping of a substrate. In certain embodiments the two forceps heads may be mechanically hinged. In other embodiments, the forceps comprise two tines movable in opposite direction relative to one another. In other embodiments, the forceps comprise one movable tine and one fixed tine. The tines may converge into one single tine at a proximal location and be separated distally in a normal state, only to close upon application of an external force on the movable tine. In some embodiments, the external force is provided by the variable interaction between one or more tines with the inner wall of the tubular sheath as the tubular sheath moves distally and interfaces with an arch of the movable tine(s).

In some embodiments, one or more additional tines in various configurations may induce folding of the substrate upon releasing and grasping.

FIG. 6 shows an embodiment with one top tine 642 and two bottom tines 641*a*, 641*b* that are parallel and offset in a latitudinal direction to the left and right side. They help cause the folding up of the left and right sides of the substrate when the substrate is grasped.

FIGS. 7A-11C show several embodiments in which one or more tines consist of curvatures that interact with a tubular sheath, thereby inducing opening and closing of the forceps as the point of interaction therebetween. Curvature changes (e.g. a slope, curve, wave) and pressure is applied to the movable tine by the tubular sheath, thereby altering the gap between the movable tine and fixed tine.

FIGS. 7A-7B show orthogonal (FIG. 7A) and side (FIG. 7B) views of the distal portion of instrument as a tubular sheath 720 interacts with an arch 743 of a movable tine 742 (at point 744) and starts to make the gap 745 between the movable tine 742 and fixed tine 741 smaller.

FIGS. 8A-8B show orthogonal (FIG. 8A) and side (FIG. 8B) views of the distal portion of the instrument as the tubular sheath 820 further interacts with the arch 843 of the movable tine 842 (at point 844) and makes the gap 845 between the movable tine 842 and fixed tine 841 even smaller. The clamp heads of movable tine 842 and fixed tine 841 have almost grasped the substrate 860.

FIGS. 9A-9B show orthogonal (FIG. 9A) and side (FIG. 9B) views of the distal portion of the instrument as clamp heads of the movable tine 942 and fixed tine 941 have grasped the substrate 960 (i.e. the two clamp heads have grasped the substrate. The point of interaction 944 of the movable tine 942 with tubular sheath 920 is at the highest point of the arch 943 of the movable tine 942.

When grasping ultra-thin substrates which are fragile due to their low thickness (e.g. less than 1000 microns, less than 100 microns, and less than 10 microns), in some embodiments the clamp heads ideally do not close to 0 microns, which may cause shear stresses that may damage the membrane. Therefore, the clamp heads may be designed to only close up to a proportional percentage of the target substrate grasping area (e.g. handle tail portion of the substrate). In an embodiment where the substrate is 10 microns thick, the clamp heads may only close between 4 to 8 microns or 40-80% of the substrate thickness, thereby providing enough pressure to frictionally hold the substrate. In an embodiment, where the substrate is 15 microns thick, the clamp heads only close between 4 to 8 microns or 13-80% of the substrate thickness, thereby providing enough pressure to frictionally hold the substrate. By not closing to 0 microns, the likelihood of cutting completely through with the clamp heads meant to grasp may be greatly reduced.

FIGS. 10A-10C shows orthogonal (FIG. 10A), side (FIG. 10B), and end/front (FIG. 10C) views of the distal portion of the instrument as the movable tine 1042 and fixed tine 1041 continue to grasp the substrate 1060.

As the tubular sheath 1020 moves distally, it interacts with the curvatures 1063a and 1063b of the substrate 1060, thereby inducing the folding of the substrate 1060 from both sides. In this embodiment, the distal end of the tubular sheath 1020 consists of a slant or taper 1064, much like a coring needle tip. This feature further induces the folding of the substrate 1060. For the curvatures 1063a and 1063b of the substrate to correctly interface the taper 1064 of the tubular sheath 1020, the arch of the movable tine 1042 has a height that is at least half of the height of an inner diameter of the tubular sheath 1020. This folds the substrate 1060 in a concave "U" shape, similarly parallel to the bottom half of the tubular sheath 1020 as seen in FIG. 10C.

In other embodiments, the height of the arch is less than half of a height of an inner diameter of the tubular sheath, thereby folding the substrate in a concave "upside down U" shape, similarly parallel to the top half of the tubular sheath. In this case, the therapeutic is ideally on the bottom surface of the substrate to be protected within the folded shape, and the taper of the tubular sheath would be in the opposite orientation (e.g. slant down) instead to create a compatible taper. If the substrate is at exactly the horizontal diameter (or semi-minor axis or semi-major axis of an oval), the substrate is not inclined to fold into a "U" shape configuration, unless the tubular sheath has a taper.

FIG. 10C further shows how the substrate 1060 width is ideally less than the inner circumference of the tubular sheath to prevent the substrate from folding/rolling onto itself, which may damage the substrate and associated therapeutic placed upon, within, or below it. In embodiments where the therapeutic consists of cells or microbubbles, this is especially the case as any overlap of the substrate onto itself could displace or damage the therapeutic. Various different shapes of the substrate and corresponding tubular sheath would make the substrate fold in different ways including but not limited to a rolling and asymmetrical rolling designs (e.g. S-shape, W-shape, etc.). At the time of implantation, when the tubular sheath 1020 moves proximally, the distal end of the tubular sheath 1020 once again interacts with the curvatures 1063a and 1063b of the substrate to slowly unfold the substrate.

FIGS. 11A-11C show orthogonal (FIG. 11A), side (FIG. 11B), and end/front (FIG. 11C) views of the distal portion of the instrument as the movable tine 1142 and fixed tine 1141 continue to grasp the substrate 1160 and pull the substrate fully within the tubular sheath 1120, thereby protecting the substrate 1160 and any therapeutic on, in, or within the substrate until the time of implantation. As the tubular sheath 1120 moves distally, it continues to interact with the curvatures 1163a and 1163b of the substrate, thereby maintaining the folding of the substrate from both sides.

Optionally, in this embodiment, a second tubular sheath 1125 is nested within at least a portion of the first tubular sheath 1120, within which the internal shaft is further nested. The second tubular sheath can be of variable thickness to vary the distance of the substrate from the inner circumference of the first tubular sheath. The distal end of the second tubular sheath 1125 further functions as a stop to limit the proximal longitudinal movement of the internal shaft in embodiments where the internal shaft is the movable component, thereby signaling the substrate has recessed fully into the first tubular sheath 1120.

In FIG. 11C, the front view of the fully retracted substrate shows further benefits of the design. First, by having a lower tine, the substrate, even when folded is offset from the inner circumference of the tubular sheath 1120, thereby minimizing scraping interactions during folding and associated shear and torsional stresses that could be damaging to an ultra-thin membrane. The addition of a second tubular sheath 1125 further adds to the offset, thereby further minimizing membrane stresses.

Second unlike conventional forceps that maximize clamping surface area by fully utilizing the inner volume to house such clamps, the described invention has clamp heads with width less than 20% of an inner diameter of the tubular sheath. This allows for ample space for the ultrathin membrane to rollup within the tubular sheath. In other embodiments, the clamp heads have a width of 20-30%, 30-40%, 40-50%, 50-60%, 60-70%, 70-80% of the inner diameter of the tubular sheath.

Third, the top tine is a curved, thin shape and the bottom tine is a thin, straight line. Thus, the clamp heads occupy less than 10% of a cross sectional inside area of the tubular sheath 1120. In other embodiments, the percentage of a cross sectional area of the clamp heads is 10-20%, 20-30%, 30-40%, 40-50%, 60-70%, 70-80%. The percentage of a cross sectional area occupied by the clamp heads may ideally remain minimal throughout the traversed longitudinal distance within the tubular sheath 1120.

Figure 12:
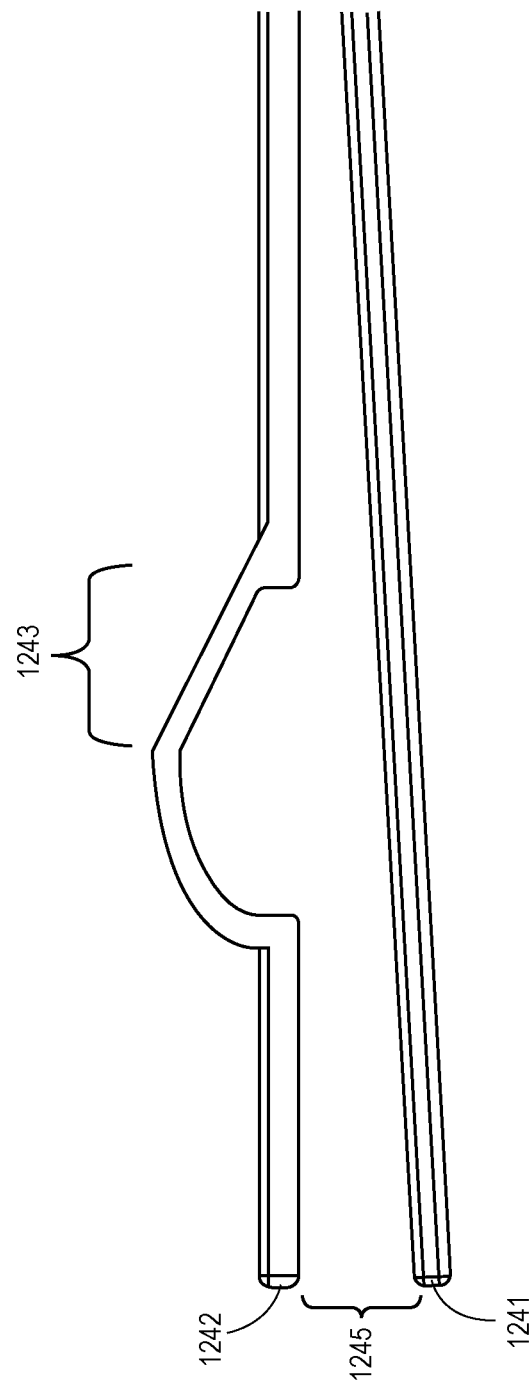
FIG. 12 is a side view of a straight line arch in accordance with an embodiment.

FIG. 12 shows the side view of the distal portion of the instrument with the arch 1243 of the movable tine 1242 in a straight line configuration. With a straight line configuration of the arch 1243 in a straight line, the interaction between the tubular sheath 1220 and movable tine 1142 changes linearly. Thus, the gap 1245 between the movable tine 1242 and fixed tine 1241 inducing opening and closing of the forceps is also linear and may be more easily controlled by the user.

Figure 13B:
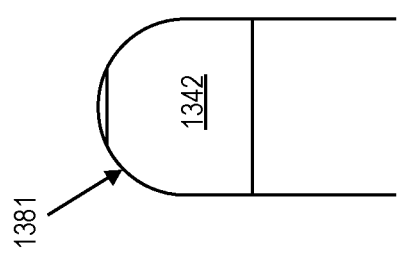
FIG. 13B is an end view showing a circular cross section of the arch of FIG. 13A.
Figure 13A:
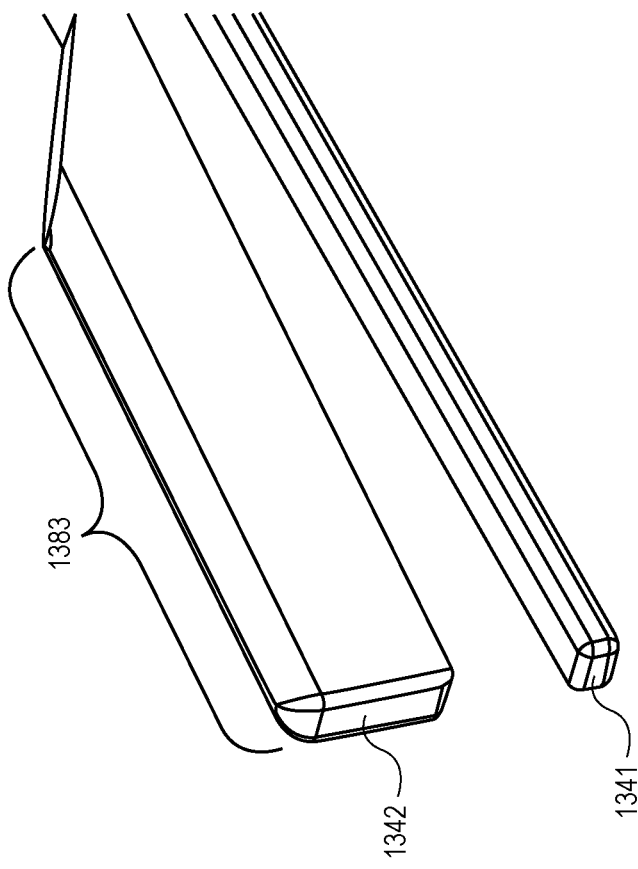
FIG. 13A is an orthogonal view of a solid arch in accordance with an embodiment.

FIGS. 13A-13B show that a longitudinal cross section of the forceps that interacts with the inner circumference of the tubular sheath may further be optimized by adding a matching cross section 1381 to automatically center the tine within a circular or oval tubular sheath to create a uniformly accurate and precise distance between the tines 1342 and 1341. The forceps may have rigid distal portions 1383 of the movable tine 1342 that are accurately dependent on the interaction with the inner circumference of the tubular sheath while having a limited flexible portion in a proximal portion allowing for opening or closing. The flexible portion may be a thinner portion of the movable tine, a shared axis between the tines, or other mechanical function to provided limited movement of the movable tine.

Figure 14:
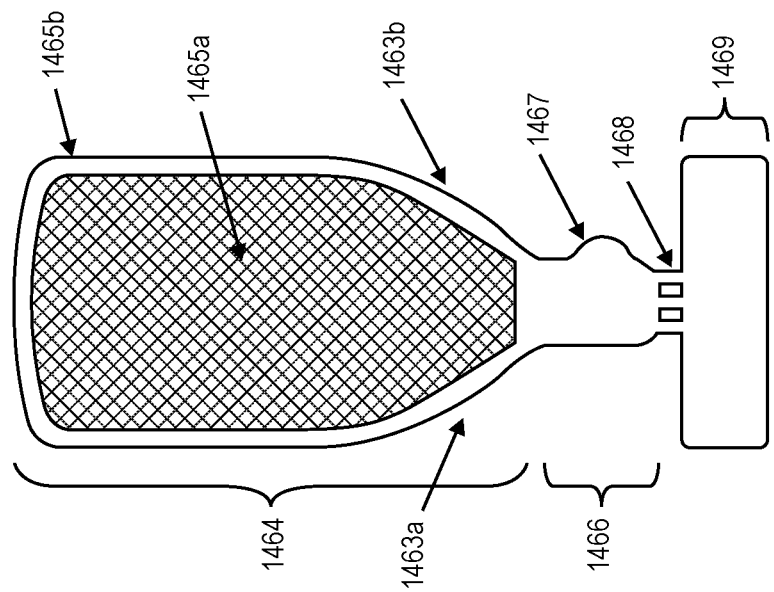
FIG. 14 illustrates a top view of a substrate in accordance with an embodiment.

FIG. 14 shows various components and sections of a substrate. The substrate includes two major pieces, the cell seeding section 1464 and tail section 1466. The cell seeding section 1464 consists of the inner cell seeding area 1465a and the surrounding perimeter 1465b on which no cells are seeded. The cell seeding section surrounding perimeter 1465b has different thickness, coating, or extruded lip to prevent cells from growing or migrating out of the cell seeding area 1465a. The cell seeding section 1464 further includes two corresponding curvatures 1463a and 1463b that interact with the inner circumference of a tubular sheath to favorably fold the substrate 1460 within the tubular sheath. The tail section 1466 is thicker and/or treated like the surrounding perimeter 1465b to prevent cells from growing or migrating out of the cell seeding area 1465a.

The tail section 1466 further includes of an orientation feature 1467 which when on the right shows that the apical cell seeded surface is on top. In other embodiments, the orientation feature 1467 can be reversed or in different shapes. If the orientation feature 1467 is on the left, the substrate is upside down and needs to be flipped to have the cells on the correct face when implanted. The tail section 1466 directly interacts with the clamp heads of the internal shaft. In some embodiments, the tail section 1466 may further include a manufacturing identification piece 1469 with manufacturing information that may be removed by cutting at a perforated cutting line 1468.

Figure 15:
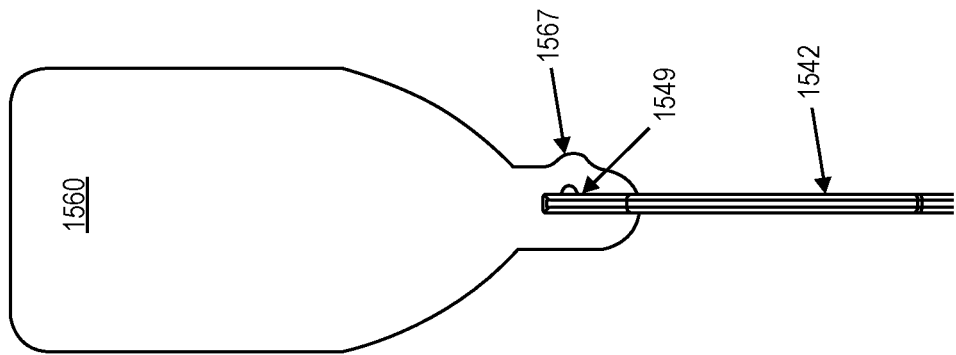
FIG. 15 illustrates a top view of a substrate being grasped by clamp heads in accordance with an embodiment.

FIG. 15 shows an embodiment with a substrate/insertion tool paired features. In this embodiment, the instrument and substrate are uniquely made to pair with each other. In one embodiment, the substrate has an orientation identifier 1567 (e.g. a bump on the right side of the handle/forceps interaction portion to show the substrate 1560 is oriented correctly with the apical cell seeded surface on top). The movable tine 1542 includes a matching small bump 1549 on the right side of the moveable tine 1542 to show that bump should be on the right for both the substrate and the tines. Such bump alignment may also be used to ensure correct longitudinal position when grasping/clamping the substrate by aligning them in parallel.

Figure 16B:
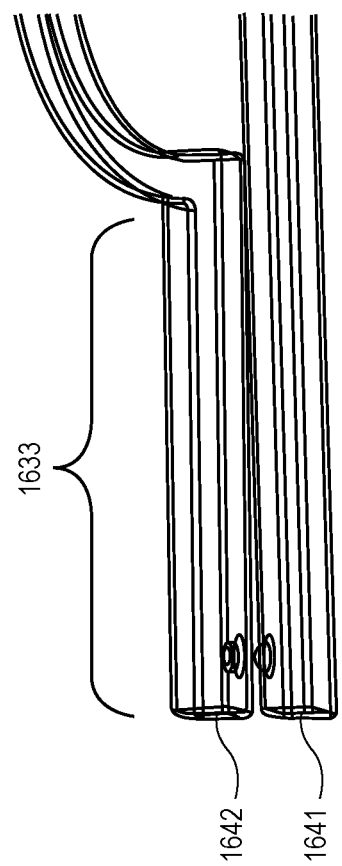
FIG. 16B illustrates clamp heads with a ball & hitch configuration in accordance with an embodiment.
Figure 16A:
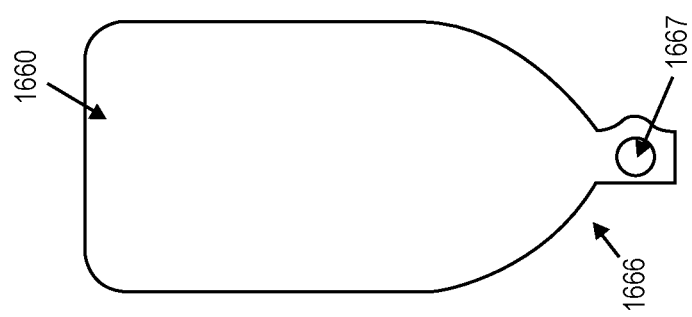
FIG. 16A illustrates a substrate with alignment features in accordance with an embodiment.

FIG. 16A shows an embodiment in which the substrate tail section 1666 further includes an opening 1667 through which the upper tine 1642 and lower tines 1641 may interact through. Not only does this allow for correct alignment to ensure correct positioning when grasping/clamping the substrate, the interaction may be used to close an electrical circuit if the tines are made of a conductive material. Such closed circuit may trigger a light or sound to convey to the user that the substrate is secure within clamp heads 1633.

FIG. 16B shows a ball/hitch type configuration on clamp heads that mate with opening 1667 of the substrate of FIG. 16A. Other corresponding shapes may alternatively be used.

Figure 17:
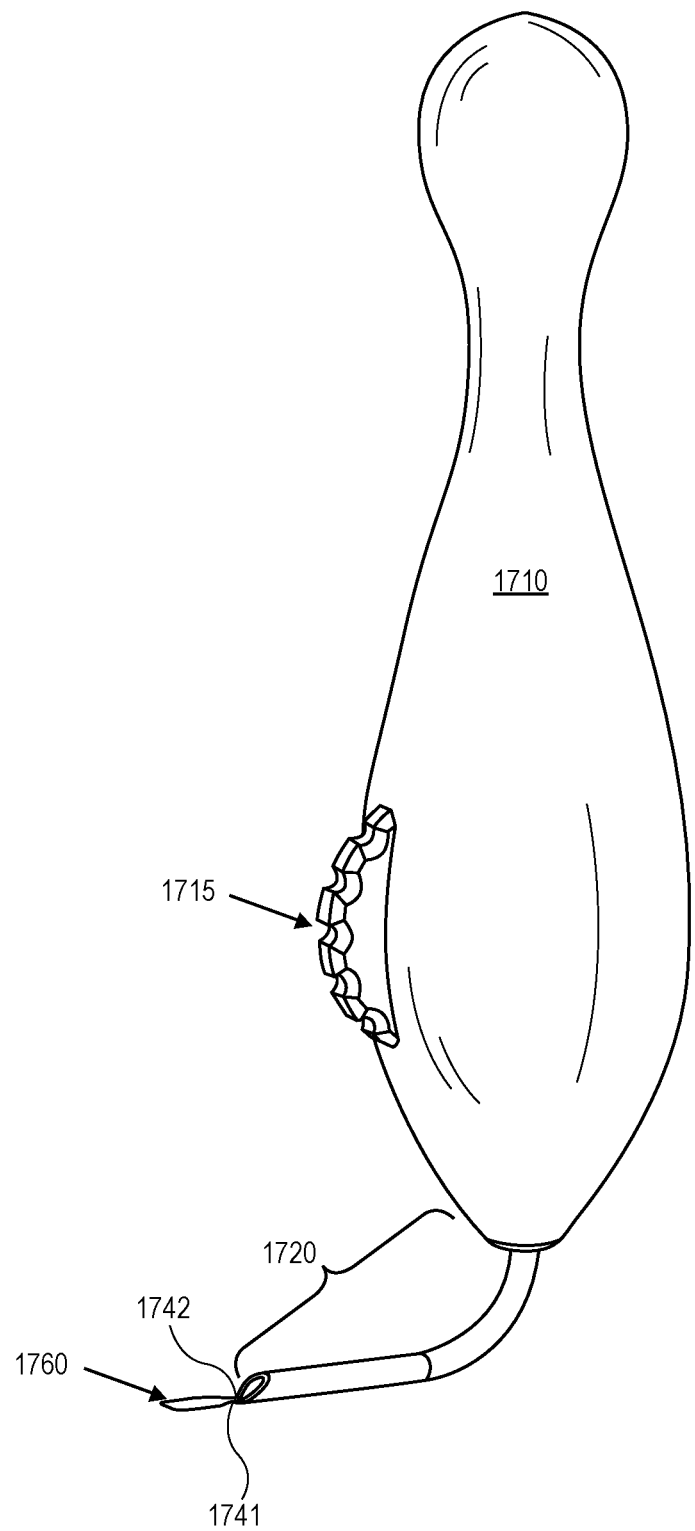
FIG. 17 illustrates an arcuate tubular sheath in accordance with an embodiment.

FIG. 17 shows an embodiment having a handpiece 1710 and control wheel 1715. Tubular sheath 1720, which projects from handpiece 1710, has various arcs and varying lengths to facilitate placement of the substrate in particular target tissue regions. For example, in ophthalmic implantations, natural variations in the axial length of the eye or the circumference of the eye may benefit from a slight curvature in the distal portion of the tubular sheath. Such curvature facilitates placement of the substrate in the sub-retinal space with a lower bleb, more posterior position and reduces the probability of retinal trauma during the delivery process, especially for eyes with longer than average axial lengths. This this embodiment, the tubular sheath 1720 is shaped like a "J", thereby allowing the surgeon to place, with upper and lower tines 1742 and 1741, the substrate 1760 in a perpendicular orientation compared to the handpiece 1710.

Thus, in several embodiments, the instruments and substrates disclosed herein protect cells on a substrate during implantation into the eye of a subject. The design of the substrate can be such that nutrients can still reach the seeded cells, but the substrate provides sufficient support to allow the cells to maintain a monolayer in vivo.

In several embodiments, specialized surgical methods to implant such substrates seeded with cells are used. These surgical procedures not only allow placement of a substrate that is specific to a particular subject, but also allow for the placement of one, two, or more substrates, depending on the severity of damage to the ocular tissue of the subject.

Additionally, substrates and methods as disclosed herein are useful for the treatment of a variety of outer retinal dystrophies. Not only are the substrates disclosed herein suitable for implantation into various places of the retina, their design which enables nutrients to reach the cells seeded thereon, the substrates are suitable for supporting the growth and function of a wide variety of cell types. By way of example only, substrates as disclosed herein could, in some embodiments, be manufactured to be seeded with photoreceptors and implanted in order to treat retinitis pigmentosa.

Various modifications and applications of embodiments of the invention may be performed, without departing from the true spirit or scope of the invention. Further, the disclosure herein of any particular feature, aspect, method, property, characteristic, quality, attribute, element, or the like in connection with an embodiment can be used in all other embodiments set forth herein. Method steps disclosed herein need not be performed in the order set forth. It should be understood that the invention is not limited to the embodiments set forth herein for purposes of exemplification, but is to be defined only by a reading of the appended claims, including the full range of equivalency to which each element thereof is entitled.

What is claimed is:

1. An instrument for implantation of a flexible, ultra-thin substrate onto a target tissue, comprising:
   a handpiece;
   a tubular sheath extended in a distal direction from said handpiece;
   an internal shaft nested within said tubular sheath and anchored with said handpiece, wherein the internal shaft comprises:
   a) a fixed tine that is parallel to the tubular sheath, the fixed tine having a clamp head; and
   b) a movable tine with a clamp head that is configured to move inwardly with respect to the clamp head of the fixed tine, the movable tine including an arch configured to variably interact with an inner wall of the tubular sheath and close the clamp heads to have a predetermined nonzero gap between the clamp heads when the clamp heads fully retract inside the tubular sheath and are not gripping anything;

a movement control mechanism configured to cause a longitudinal movement of said tubular sheath with respect to said handpiece and thus cause the arch to variably interact with the inner wall of the tubular sheath.

2. The instrument of claim 1, wherein the arch has a height that is at least half of a height of an inner diameter of the tubular sheath.

3. The instrument of claim 1, wherein the arch of the movable tine includes a slope, a curve, or a wave pattern.

4. The instrument of claim 1, wherein the predetermined gap is between 2 microns and 12 microns.

5. The instrument of claim 4, wherein the predetermined gap is between 4 microns and 8 microns.

6. The instrument of claim 1, further comprising:
a substrate having a handle with a thickness;
wherein the predetermined gap is between 10% and 100% of the substrate handle thickness.

7. The instrument of claim 6, further comprising:
cells on or within one or more surfaces of the substrate.

8. The instrument of claim 1, wherein a cross sectional area of the clamp heads is less than 10% of an internal cross sectional area of the tubular sheath.

9. The instrument of claim 1, wherein a width of the clamp heads is less than 20% of an inner diameter of the tubular sheath.

10. The instrument of claim 1, wherein the tubular sheath is tapered at a distal portion.

11. The instrument of claim 10, wherein the taper of the tubular sheath is configured to induce a folding of a substrate when the clamp heads gripping the substrate retract inside the tubular sheath.

12. The instrument of claim 11, wherein the tubular sheath is a first tubular sheath, the instrument further comprising:
a second tubular sheath nested and fixed within at least a portion of the first tubular sheath, within which the internal shaft is further nested such that the tines are offset from a side wall of the first tubular sheath when the clamp heads are gripping the substrate.

13. The instrument of claim 1, wherein a cross section of the arch of the movable tine includes a curvature matching an interfacing inner circumference of the tubular sheath.

14. The instrument of claim 1, wherein the tubular sheath is a first tubular sheath, the instrument further comprising:
a second tubular sheath nested within at least a portion of the first tubular sheath, within which the internal shaft is further nested.

15. The instrument of claim 14, wherein the second tubular sheath is configured to prevent the clamp heads from retracting beyond a fixed point within the first tubular sheath.

16. The instrument of claim 1, wherein the clamp heads include an orientation confirmation feature.

17. The instrument of claim 16, wherein the orientation confirmation feature includes a bump.

18. The instrument of claim 1, wherein the tubular sheath has a circular or oval cross-section.

19. The instrument of claim 1, wherein the tubular sheath is transparent or translucent.

20. The instrument of claim 1, wherein said internal shaft is anchored with the handpiece so as to not move longitudinally with respect to the handpiece when the tubular sheath is moved.

* * * * *